United States Patent [19]

Bindra et al.

[11] Patent Number: 4,749,687
[45] Date of Patent: Jun. 7, 1988

[54] RENIN INHIBITORS CONTAINING STATINE OR DERIVATIVES THEREOF

[75] Inventors: Jasit S. Bindra; Edward F. Kleinman, both of Groton; Robert L. Rosati, Stonington, all of Conn.

[73] Assignee: Pfizer Inc., New York, N.Y.

[21] Appl. No.: 839,010

[22] Filed: Mar. 10, 1986

Related U.S. Application Data

[63] Continuation-in-part of Ser. No. 763,768, Aug. 8, 1985, abandoned, which is a continuation of Ser. No. 588,279, Mar. 12, 1984, abandoned.

[30] Foreign Application Priority Data

Mar. 11, 1985 [CA] Canada ............................. 476191

[51] Int. Cl.$^4$ .................. A61K 37/43; C07K 7/06; C07K 5/08; C07K 5/10
[52] U.S. Cl. .................................. 514/18; 514/16; 514/17; 530/328; 530/329; 530/330
[58] Field of Search ................. 530/328, 329, 330; 514/16, 17, 18

[56] References Cited

U.S. PATENT DOCUMENTS

| 4,304,994 | 5/1983 | Veber et al. | 260/112.5 |
|---|---|---|---|
| 4,374,829 | 2/1983 | Harris et al. | 424/177 |
| 4,424,207 | 1/1984 | Szelke et al. | 424/177 |
| 4,455,303 | 6/1984 | Burton | 424/177 |
| 4,470,971 | 9/1984 | Boger et al. | 424/177 |
| 4,478,826 | 10/1984 | Veber et al. | 424/177 |
| 4,478,827 | 10/1984 | Haber | 424/177 |
| 4,479,941 | 10/1984 | Veber et al. | 424/177 |
| 4,481,192 | 11/1984 | Cazaubon et al. | 424/177 |
| 4,485,099 | 11/1984 | Boger et al. | 424/177 |
| 4,609,643 | 9/1986 | Szelke et al. | 530/328 |
| 4,650,661 | 3/1987 | Szelke et al. | 530/328 |

FOREIGN PATENT DOCUMENTS

| 0012401 | 12/1979 | European Pat. Off. |
| 0111266 | 12/1980 | European Pat. Off. |
| 0035383 | 2/1981 | European Pat. Off. |
| 0077028 | 10/1982 | European Pat. Off. |
| 0114993 | 12/1983 | European Pat. Off. |

Primary Examiner—Delbert K. Phillips
Attorney, Agent, or Firm—Peter C. Richardson; Lawrence C. Akers; Paul H. Ginsburg

[57] ABSTRACT

A series of novel peptide and polypeptide derivatives containing statine or derivatives thereof (e.g., aminostatine, cyclostatine) are disclosed that are useful for inhibiting the angiotensinogen-cleaving action of the enzyme renin. Of particular interest are compounds possessing the N-terminal sequence -Pro-Phe-His-Sta-Lys with the terminal proline nitrogen bonded to an amino-protecting acyl moiety or compounds possessing the N-terminal sequence -R-Phe-His-Sta-Lys- wherein R represents an amino protecting acyl group.

49 Claims, No Drawings

4,749,687

RENIN INHIBITORS CONTAINING STATINE OR DERIVATIVES THEREOF

This is a continuation-in-part of application Ser. No. 763,768 filed on Aug. 8, 1985 which is a continuation of application Ser. No. 588,279 filed on Mar. 12, 1984, both now abandoned.

BACKGROUND OF THE INVENTION

The proteolytic enzyme renin, which has a molecular weight of about 40,000, is produced in and secreted into the blood by the kidney. It is known to be active in vivo in cleaving the naturally-occurring plasma glycoprotein angiotensinogen, in the case of human angiotensinogen at the bond between the leucine (10th) and valine (11th) amino acid residues at the N-terminal end of the angiotensinogen:

Asp—Arg—Val—Tyr—Ile—His—Pro—Phe—His—Leu—Val—Ile—His—Ser—Glu—
 1    2    3    4    5    6    7    8    9    10   11   12   13   14   15

The circulating N-terminal decapeptide (angiotensin I) formed by the above cleaving action of renin is subsequently broken down by the body to an octapeptide known as angiotensin II. Angiotensin II is known to be a potent pressor substance, i.e. a substance that is capable of inducing a significant increase in blood pressure, and is believed to act by causing the constriction of blood vessels and the release of the sodium-retaining hormone aldosterone from the adrenal gland. Thus, the renin-angiotensinogen system has been implicated as a causative factor in certain forms of hypertension.

One means of alleviating the adverse effects of the functioning of the renin-angiotensinogen system is the administration of a substance capable of inhibiting the angiotensinogen-cleaving action of renin. A number of such substances are known, including antirenin antibodies, pepstatin and naturally-occurring phospholipid compounds. European patent application No. 45,665 (published Feb. 2, 1982) discloses a series of renin-inhibiting polypeptide derivatives of the formula X-Y-Pro-Phe-His-A-B-Z-W in which X may be hydrogen or an amino-protecting group, Y may be absent, B is a lipophilic amino acid residue, Z is an aromatic amino acid residue, W may be hydroxyl and A may be, inter alia, $$-NH-\underset{\underset{}{}}{CH}-\underset{\underset{OH}{|}}{CH}-CH_2-\underset{\underset{}{}}{CH}-\overset{O}{\overset{\|}{C}}-$$
$$\phantom{-NH-}\overset{R^1}{|}\phantom{-CH-}\overset{R^2}{|}$$

with each of $R^1$ and $R^2$ being a lipophilic or aromatic side chain. According to the definitions set forth in this published patent application, it is not contemplated that either A or Z could be statine or that B could be lysine.

European Patent Application No. 77,028 (published Apr. 20, 1983) discloses a series of renin-inhibiting polypeptide compounds having a non-terminal statine or statine derivative residue. Included within this series are compounds having a phenylalanine-histidine-statine sequence. However, this published patent application does not disclose the placement of lysine immediately after the -Phe-His-Sta- sequence.

SUMMARY OF THE INVENTION

We have now discovered that certain novel compounds are useful as renin-inhibiting agents. This series of novel compounds comprises polypeptides and polypeptide derivatives of the formula $$R-W-W^1-NH-\underset{\underset{R^3}{|}}{CH}-\overset{R^2}{\overset{|}{CH}}-CH_2-COR^1 \qquad I$$

and the pharmaceutically acceptable salts thereof, wherein

R is selected from the group consisting of hydrogen, an amino-protecting acyl moiety having a molecular weight of less than 500, proline, amino-protected proline, pyroglutamic acid and amino-protected pyroglutamic acid;

W is phenylalanine, histidine, leucine, tyrosine, and 1-naphthylalanine;

$W^1$ is phenylalanine, histidine, leucine, tyrosine or norleucine; with the nitrogen group of the peptide link between W and $W^1$ optionally being substituted by alkyl of from 1 to 4 carbon atoms when W is phenylalanine and $W^1$ is histidine;

$R^2$ is selected from the group consisting of hydrogen, alkyl of from 1 to 6 carbon atoms, phenyl, cycloalkyl of from 4 to 7 carbon atoms, phenylalkyl of from 7 to 9 carbon atoms and cycloalkyl(alkylene) of from 5 to 10 carbon atoms;

$R^3$ is selected from the group consisting of hydroxyl, amino, —$NHR^9$, —$NHCOR^9$, —$OR^9$ and —O-$COR^9$, with $R^9$ being alkyl of from 1 to 4 carbon atoms; and $R^1$ is selected from the group consisting of
(a) -A-E-B,
with A being lysine, proline, or additionally, when $R^3$ is amino or when the nitrogen of the peptide linkage between W and $W^1$ is substituted by alkyl of 1 to 4 carbon atoms, A is isoleucine.

E being selected from the group consisting of phenylalanine, glycine, alanine, valine, leucine, isoleucine, lysine, ornithine, arginine, aspartic acid, gamma-esterified aspartic acid, glutamic acid and delta-esterified glutamic acid, B being selected from the group consisting of —$OR^4$, —$NR^4R^5$, -glutamic acid (—$OR^4$)$_2$, -glutamic acid (—$OR^4$) (—$NR^4R^5$) and -glutamic acid (—$NR^4R^5$)$_2$, and $R^4$ and $R^5$ each being selected from the group consisting of hydrogen, alkyl of from 1 to 4 carbon atoms, phenylalkyl of from 7 to 9 carbon atoms and cycloalkyl(alkyl) of from 5 to 10 carbon atoms, and $$\text{(b) } -X-\underset{\underset{}{}}{N}-\overset{R^a}{\overset{|}{CH}}-(CH_2)_n-Q-\overset{Z^1}{\overset{|}{CH}}-(CH_2)_m-Y,$$

with X being absent or selected from the group consisting of alanine, isoleucine, lysine, proline, ornithine, arginine, N-(alkyl of from 1 to 4 carbon atoms)-lysine, N,N-di(alkyl of from 1 to 4 carbon atoms)-lysine, N-(alkyl of from 1 to 4 carbon atoms)-ornithine and N,N-di(alkyl of from 1 to 4 carbon atoms)-ornithine, $R^a$ being hydrogen or alkyl of from 1 to 4 carbon atoms, Z and $Z^1$ each being selected from the group consisting of hydrogen, alkyl of from 1 to 6 carbon atoms, cycloalkyl of from 4 to 7 carbon atoms, cycloalkyl(alkylene) of from 5 to 10 carbon atoms and phenylalkyl of from 7 to 9 carbon atoms, n and m each being 0 or an integer from 1 to 6, Q being selected from the group consisting of

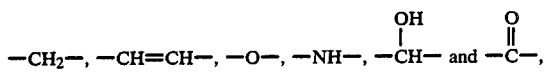

Y being selected from the group consisting of methyl, phenyl, imidazolyl, $-COOR^6$, $-CONR^6R^7$, glutamic acid, $-CO$-glutamic acid-$(-OR^6)_2$, $-CO$-glutamic acid $(-OR^6)$-$(-NR^6R^7)$ and $-CO$-glutamic acid$(-NR^6R^7)_2$, or $NR^6R^7$ and $R^6$ and $R^7$ each being selected from the group consisting of hydrogen, alkyl of from 1 to 4 carbon atoms, phenylalkyl of from 7 to 9 carbon atoms and cycloalkyl(alkylene) of from 5 to 10 carbon atoms (c) $-NH_2$,
(d) alkoxy of from 1 to 4 carbon atoms,
(e) 4-benzylpiperazin-1-yl,
(f) 1,2,3,4-tetrahydroquinolin-1-yl,
(g) 1,2,3,4-tetrahydroisoquinolin-2-yl,
(h) 1,2,3,4-tetrahydro-3-aminocarbonylisoquinolin-2-yl
(i) 1,2,3,4-tetrahydro-3-methoxycarbonylisoquinolin-2-yl,
(j) 1,2,3,4,5,6,7,8-decahydro-3-methoxycarbonylisoquinolin-2-yl,
(k) 2-methoxycarbonyl-pyrrolidin-1-yl,
(l) 2-aminocarbonyl-pyrrolidin-1-yl,
(m) 4-phenylmethyl-piperidin-1-yl,
(n) -proline-B, with B being as defined above, or
(o) -lysine-B, with B being as defined above.

It will be apparent to those skilled in the art that the above formula also describes a polypeptide which can be represented by the alternative formula

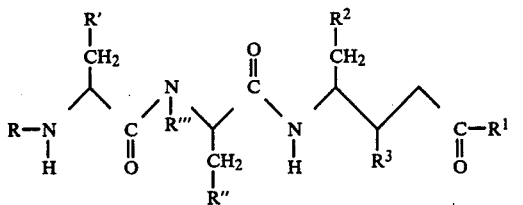

wherein R, $R^1$, $R^2$ and $R^3$ are as previously described and R' is phenyl, hydroxyphenyl, 4-imidazolyl, amine $C_{2-4}$ alkyl, $C_1$ to $C_4$ straight or brached chain alkyl, or naphthyl; R" is phenyl, hydroxyphenyl, 4-imidazolyl, amine $C_{2-4}$ alkyl, or $C_{1-4}$ straight or brached chain alkyl and R'" is hydrogen or $C_{1-4}$ alkyl.

Of particular interest are those compounds wherein R is an amino protecting acyl moiety or amino-protected proline, W is phenylalanine, $W^1$ is histidine bonded to W in a peptide link, $R^2$ is isobutyl or cyclohexyl(methylene), $R^3$ is hydroxy and $R^1$ is (a), (b) or (n) above, with A being lysine where $R^1$ is (a) and X being lysine or proline when $R^1$ is (b).

Of interest also are those compounds wherein W is phenylalanine, $W^1$ is N-alkyl histidine, $R^2$ is isobutyl or cyclohexyl(methylene), $R^3$ is hydroxy and $R^1$ is (a), (b) or (n) above with A being lysine where $R^1$ is (a) and X being lysine or proline when $R^1$ is (b).

Also of interest are those compounds wherein $R^1$ is (b) with X being alanine, proline, isoleucine or lysine Z being isobutyl or hydrogen, Q being

$Z^1$ being hydrogen, n and m each being O or the sum of n and m being from 0 to 3, $R^a$ being hydrogen, Q being $-CH-$ and Y being $COOR^6$ or $-CONR^6R^7$.

Of interest also are those compounds wherein $R^1$ is (b) with X being absent, $Z^1$ being hydrogen or benzyl, Z being alkyl of from 1 to 6 carbon atoms, Q being $-CH_2-$ or $-NH-$, m and n each being zero or the sum of n and m being from 0 to 3, $R^a$ being hydrogen, and Y being $COOR^6$ or $CONR^6R^7$.

Other compounds of interest are those where W is phenylalanine, $W^1$ is histidine, $R^2$ is isobutyl, $R^3$ is amino, and $R^1$ is (a) with A being isoleucine.

Still other compounds of interest are those wherein $R^1$ is (b) with X being absent, $R^a$ being methyl, Z and $Z^1$ each being hydrogen, m and n each being O, Q being $CH_2$ and Y being $NR^6R^7$.

DETAILED DESCRIPTION OF THE INVENTION

The compounds of this invention exhibit antihypertensive activity in vivo in mammals, including humans. At least a substantial portion of this activity results from their ability to inhibit the cleavage of angiotensinogen by renin. Although we do not wish to be limited by the following theory of mechanism, it is likely that the mechanism of the renin-inhibiting activity of the compounds of the invention is their selective binding (as compared to angiotensinogen) to renin. Because of their low molecular weights the compounds of the invention exhibit favorable solubility characteristics in aqueous media, thus making oral administration feasible, and can be synthesized at a commercially realistic cost. The compounds of the present invention are also useful as diuretics.

By "pharmaceutically acceptable" salts is meant those salts which are non-toxic at the dosages administered. Since compounds of the invention may contain both basic and acidic groups, both acid addition and base addition salts are possible. Pharmaceutically acceptable acid addition salts include e.g. the hydrochloride, hydrobromide, hydroiodide, sulfate, bisulfate, phosphate, acid phosphate, acetate, lactate, maleate, mesylate, fumarate, citrate, acid citrate, tartrate, bitartrate, succinate, gluconate and saccharate salts. Pharmaceutically acceptable base addition salts include e.g. the sodium, potassium, calcium and magnesium salts. Conventional methods of forming acid addition and base addition salts may be employed.

The group R at the N-terminal end of formula I, which is bonded to the alpha-nitrogen of the residue W, is selected from the group consisting of hydrogen, amino-protecting acyl moieties having a molecular weight of less than 500, proline, amino-protected proline, pyroglutamic acid and amino-protected pyroglutamic acid. It is to be understood that the amino-protecting group of amino-protected proline or amino-protected pyroglutamic acid is also an amino-protecting acyl moiety having a molecular weight of less than 500. The term "amino-protecting acyl moieties" refers to those acyl groups that are capable of substantially inhibiting reaction at the alpha-nitrogen of W (or proline or pyroglutamic acid) in vivo after oral administration. R has a molecular weight of less than 500 in order to prevent an excessive detrimental effect on solubility characteristics. Examples of suitable amino-protecting acyl moieties are well known to those skilled in the art, e.g. the t-butyloxycarbonyl, t-butylacetyl, benzyloxycarbonyl, t-butyluriedo, (tris-hydroxy)-(t-butyluriedo) and phenoxyacetyl moieties. Preferably, R is of the formula

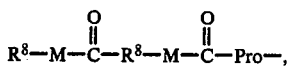

with M being selected from the group consisting of

—O—, CH$_2$—, —NH— and —SO$_2$NH— and R$^8$ being selected from the group consisting of alkyl of from 1 to 6 carbon atoms, phenyl, phenylalkyl of from 7 to 9 carbon atoms and cycloalkyl(alkylene) of from 5 to 10 carbon atoms.

As used herein, the expressions -glutamic acid-(—OR$^4$)(—NR$^4$R$^5$) and —CO-glutamic acid(—OR$^6$)(—NR$^6$R$^7$) refer both to C-terminal groups that are amidified at the delta-carbon of glutamic acid and C-terminal groups that are esterified at the delta-carbon of glutamic acid. As stated earlier, one preferred group of compounds of the invention consists of those wherein R$^3$ is hydroxyl and R$^2$ is isobutyl or cyclohexyl(methylene), more preferably the latter, so that

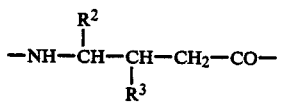

becomes -statine- or -cyclostatine-, R is an amino-protecting acyl moiety having a molecular weight of less than 500 or amino-protected proline, W is phenylalanine, W$^1$ is histidine bonded to W in a peptide link and R$^1$ is Lys-E-B, Pro-B or

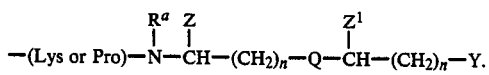

Placement of a lysine residue (instead of, for example, a leucine, isoleucine, valine or alanine residue) immediately after -phenylalanine-histidine-(statine or cyclostatine)- surprisingly results in a dramatic increase in the duration of in vivo renin-inhibiting activity.

Another preferred group of the compounds of the invention consists of those wherein R is an amino-protecting acyl moiety having a molecular weight of less than 500 or amino-protected proline, W is phenylalanine, W$^1$ is histidine bonded to W in a peptide link, R$^3$ is hydroxyl, R$^2$ is isobutyl or cyclohexyl(methylene), more preferably the latter, and R$^1$ is

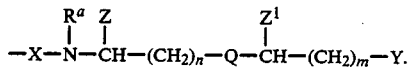

Reduction of the peptidic nature of the molecular structure adjacent its C-terminal end tends to improve absorption into the blood stream after oral aministration. Note that when n and m are each zero, Z is isobutyl, Q is

Z$^1$ is hydrogen and Y is carboxyl, R$^1$ becomes -X-statine.

Also preferred are those compounds wherein the histidine moiety is N-alkylated. Especially preferred compounds of this class are those possessing the sequence Phe-N-methyl-His-(statine or cyclostine).

Particularly valuable are the following compounds and their pharmaceutically acceptable salts:

[N-(t-butyloxycarbonyl)-proline]-phenylalanine-histidine-cyclostatine-lysine-phenylalanine;

[N-(t-butyloxycarbonyl)-phenylalanine]-histidine-cyclostatine-lysine-phenylalanine;

[N-(t-butyloxycarbonyl)-phenylalanine]-histidine-statine-lysine-phenylalanine;

[N-(t-butyloxycarbonyl)-phenylalanine]-histidine-statine-alanine-statine-glutamic acid;

[N-(t-butyloxycarbonyl)-phenylalanine]-histidine-statine-isoleucine-[amino(n-butyric acid)];

[N-(t-butyloxycarbonyl)-phenylalanine]-histidine-cyclostatine-[amino(2-sec butyl-ethylene)]-phenylalanine;

[N-(t-butyloxycarbonyl)-phenylalanine]-histidine-statine-[amino(2-sec butyl-ethylene)]-phenylalanine;

[N-(t-butyloxycarbonyl)-phenylalanine]-histidine-cyclostatine-[amino(2-sec butyl-ethylene)]-histidine.

[N-(t-butyloxycarbonyl)-phenylalanine]-histidine-cyclostatine-1,2,3,4-tetrahydro-2-isoquinoline;

[N-(t-butyloxycarbonyl)-proline]-phenylalanine-histidine-cyclostatine-1,2,3,4-tetrahydro-2-isoquinoline;

[N-(t-butyloxycarbonyl)-phenylalanine]-histidine-cyclostatine-proline-[amino(n-pentylene)amine];

[N-(t-butyloxycarbonyl)-phenylalanine]-histidine-cyclostatine-proline methyl ester;

[N-(t-butyloxycarbonyl)-phenylalanine]-histidine-cyclostatine ethyl ester;

[N-(t-butyloxycarbonyl)-phenylalanine]-histidine-cyclostatine-proline-NH$_2$;

[N-(t-butyloxycarbonyl)-phenylalanine]-histidine-cyclostatine-NH$_2$;

[N-(t-butyloxycarbonyl)-phenylalanine]-histidine-cyclostatine-lysine-statine.

[N-(t-butyloxycarbonyl)-phenylalanine]-N-methyl-histidine-statine-lysine-phenylalanine;

[N-(t-butyloxycarbonyl)-phenylalanine]-N-methyl-histidine-statine-lysine-phenylalanine; and

[N-(t-butyloxycarbonyl)-phenylalanine]-histidine-cyclostatine-N-methyl-N-(3-dimethyl-aminoprop-1-yl)-amide.

The compounds of the invention may be prepared by methods familiar to those skilled in the art. The basic sub-unit of the preferred chemical synthesis is the acylation of the unprotected alpha-amino group of an amino acid residue with an amino acid having an activated (for acylation purposes) carboxylic function and a suitable protecting group bonded to its own alpha-nitrogen to form a peptide bond between the two amino acid residues, followed by the removal of said protecting group. This synthesis sub-unit of coupling-deblocking is performed repeatedly to build up the polypeptide, starting from the C-terminal end of the molecular structure and working to the N-terminal end. The alpha-amino acids utilized to synthesize the compounds of the present invention are commercially available (as free acids, salts or esters, etc.) in both alpha-amino protected and alpha-amino unprotected forms. Statine is commercially available as N-(t-butyloxycarbonyl)-statine; additionally, statine may be prepared (as a free acid or ester) in both the gamma-amino protected and gamma-amino unprotected forms by methods set forth in the literature (see e.g. U.S. Pat. No. 4,397,786 and Rich, D. H. et al., *Jour. Org. Chem.*, 43, pp. 3624 et seq. (1978). When desired, an appropriate N-unprotected amino acid analogue (free acid, salt or ester, etc.) such as 4-aminobutyric acid, 4-amino-valeric acid or 4-amino-4-sec butyl-butyric acid is used as a reactant in the first coupling step. Appropriate derivatives of statine may be prepared by conventional synthetic methods. Thus, for example, the compound

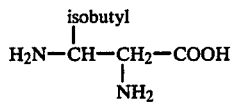

which is referred to herein as aminostatine, may be prepared in a form with both amino groups protected by reacting an amino-protected statine ester with a sulfonyl chloride to form a sulfonate ester, reacting the sulfonate ester with sodium azide to form an amino-protected 4-isobutyl-2-butenoic acid ester and an amino-protected 4-isobutyl-3-azido-butyric acid ester, reacting the alkenoic compound with a primary amine and/or hydrogenating the azido compound and then reducing the resulting intermediate compound with an alkali metal hydride in the presence of an aldehyde to form (in both cases) a 4-isobutyl-3-sec amino derivative of butyric acid, hydrogenating this 4-isobutyl-3-sec amino derivative of butyric acid and then reacting the resulting compound with an acyl halide under basic conditions. N-protected compounds

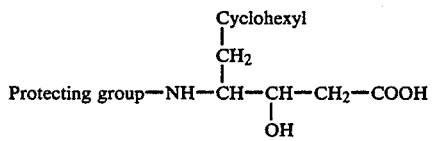

which are referred to herein as N-protected cyclostatine compounds, may be prepared by hydrogenating the corresponding N-protected-4-amino-4-phenylmethyl-3-hydroxy-butyric acid compound, which in turn may be prepared in the manner set forth by Rich, D. H. et al., *Jour. Med. Chem.*, 23(1), pp. 27–33 (1980).

The reduced peptide link (C(O)—replaced by —CH$_2$—) in a compound of the invention wherein R$^1$ is

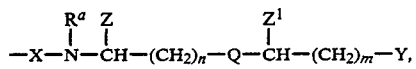

n is at least 1 and Q is —NH— may be formed by reducing an aldehyde of the formula

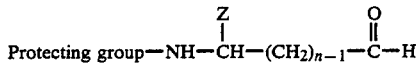

in the presence of an amino ester of the formula

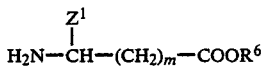

wherein R$^6$ is other than hydrogen.

The activity of the compounds of the present invention as inhibitors of the angiotensinogen-cleaving activity of renin may be determined by studying (1) their ability to inhibit the angiotensinogen-cleaving activity of renin in vitro and (2) their ability to antagonize the exogenous renin-induced pressor response in vivo.

The compounds of the present invention can be administered as antihypertensive agents by either the oral or parenteral routes of administration, with the former being preferred for reasons of patient convenience and comfort. In general, these antihypertensive compounds are normally administered orally in dosages ranging from about 0.1 mg. to about 10 mg. per kg. of body weight per day; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

The novel compounds of the invention can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosage.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The following examples illustrate the invention but are not to be construed as limiting the same.

In the following examples, the abbreviation "im" refers to a histidine moiety protected at the imidazole nitrogen by an appropriate protecting group.

EXAMPLE 1

[N-(t-butyloxycarbonyl)-Phe]-His-Sta-Lys-Phe

A.

[N-Alpha-(t-butyloxycarbonyl)-N-epsilon-benzyloxycarbonyl-Lysine]-Phenylalanine Benzyl Ester N-hydroxybenzotriazole (162 mg, 1.2 mmoles), N-methyl-morpholine (101.2 mg.,) 1 mmole), L-phenylalanine benzyl ester p-toluenesulfonate (428 mg., 1 mmole), N-alpha-(t-butyloxycarbonyl)-N-epsilon-benzyloxycarbonyl-L-lysine (456 mg., 1.2 mmoles) and 1-cyclohexyl-3-(2-morpholinoethyl)-carbodiimide metho-p-toluene sulfonate (635 mg., 80% pure, 1.2 mmoles) were sequentially dissolved in methylene chloride (50 ml.) at 0° C. and the resulting solution stirred for 19 hours at 20° C. The reaction mixture was then washed consecutively with 75 ml. of 5.5% aqueous HCl, 75 ml. of saturated aqueous NaHCO$_3$ and 75 ml. of brine, and dried over anhydrous MgSO$_4$. After filtration and evaporation, 669 mg. of crude product was obtained as a foam ($^1$H NMR, CDCl$_3$, 1.5 delta, 9 H s [BOC]). This crude product was used without further purification in the next step.

B (N-Epsilon-benzyloxycarbonyl-Lysine)Phenylalanine Benzyl Ester Hydrochloride

[N-Alpha-(t-butyloxycarbonyl)-N-epsilon-benzyloxycarbonyl-lysine]-phenylalanine benzyl ester from step A(650 mg., 1 mmole) was dissolved in 7 ml. of 3.7N HCl/dioxane and allowed to stand for one hour at 20° C. The solution was then evaporated to dryness to afford 583 mg. of crude product as an oil which was used without purification in the next step ($^1$H NMR, CD$_3$OD, 5.2 delta, 2H s[benzyl CH$_2$]).

C.

[N-(t-butyloxycarbonyl)-Statine]-(N-epsilon-benzyloxycarbonyl-Lysine)-Phenylalanine Benzyl Ester (N-Epsilon-benzyloxycarbonyl-lysine)-phenylalanine benzyl ester hydrochloride from step B (583 mg., 1 mmole), N-methyl-morpholine (101.2 mg., 1 mmole), N-(t-butyloxycarbonyl)-statine (330 mg., 1.2 mmoles), N-hydroxybenzotriazole (162 mg., 1.2 mmoles) and 1-cyclohexyl-3-(2-morpholinoethyl)-carbodiimide metho-p-toluene sulfonate (635 mg., 80% pure, 1.2 mmoles) were sequentially dissolved in 50 ml. of methylene chloride at 0° C. and the resulting solution stirred for 19 hours at 20° C. The reaction mixture was worked up as in step A to yield 760 mg. of crude product which was used without further purification in the next step ($^1$H NMR, CDCl$_3$, 1.5 delta, 9H s[BOC]).

D.

Statine-(N-epsilon-benzyloxycarbonyl-Lysine)-Phenylalanine Benzyl Ester Hydrochloride

[N-(t-butyloxycarbonyl)-statine]-(N-epsilon-benzyloxycarbonyl-lysine)-phenylalanine benzyl ester from step C (760 mg., 1 mmole) was dissolved in 10 ml. of 3.7N HCl/dioxane and allowed to stand for one hour at 20° C. This reaction mixture was worked up as in step B to afford 620 mg. of crude product as a foam ($^1$H NMR, CD$_3$OD, 5.2 delta, 2H s[benzyl CH$_2$]), which was used without purification in the next step.

E.

[N-Alpha-(t-butyloxycarbonyl)-N-im-(t-butyloxycarbonyl)-Histidine]-Statine-(N-epsilon-benzyl-oxycarbonyl-Lysine)-Phenylalanine Benzyl Ester Statine-(N-epsilon-benzyloxycarbonyl-lysine)-phenylalanine benzyl ester hydrochloride from step D (600 mg., 0.857 mmoles), N-methyl-morpholine (86.7 mg., 0.857 mmoles), N-alpha-(t-butyloxycarbonyl)-N-im-(t-butyloxycarbonyl)-L-histidine (365 mg., 1.03 mmoles), N-hydroxybenzotriazole (135 mg., 1.03 mmoles) and 1-cyclohexyl-3-(2-morpholinoethyl)-carbodiimide metho p-toluene sulfonate (545 mg., 1.03 mmoles) were sequentially dissolved in 50 ml. of methylene chloride at 0° C. and allowed to stir for 19 hours at 20° C. This reaction mixture was worked up as in step A to yield 770 mg. of crude product as a foam ($^1$H NMR, CDCl$_3$, 1.5 delta, 2H s[BOC]and 1.6 delta, 9H s[BOC]), which was used in the next step without further purification.

F.

Histidine-Statine-(N-epsilon-benzyloxycarbonyl-Lysine)-Phenylalanine Benzyl Ester Dihydrochloride

[N-Alpha-(t-butyloxycarbonyl)-N-im-(t-butyloxycarbonyl)-histidine]-statine-(N-epsilon-benzyloxycarbonyl-lysine)-phenylalanine benzyl ester from step E (770 mg., 0.85 mmole) was dissolved in 10 ml. of 3.7N HCl/dioxane and allowed to stand for 1.5 hours at 20° C. The reaction mixture was worked up as in step B to afford 602 mg. of crude product as a foam ($^1$H NMR, CD$_3$OD, 5.2 delta, 2H s [benzyl CH$_2$]), which was used in the next step without purification.

G.

[N-(t-butyloxycarbonyl)-Phenylalanine]-Histidine-Statine-(N-epsilon-benzyloxycarbonyl-Lysine)-Phenylalanine Benzyl Ester Histidine-statine-(N-epsilon-benzyloxycarbonyl-lysine)-phenylalanine benzyl ester dihydrochloride from step F (602 mg., 0.689 mmoles), N-methyl-morpholine (139 mg., 1.38 mmoles), N-(t-butyloxycarbonyl)-L-phenylalanine (219 mg., 0.827 mmoles), N-hydroxybenzotriazole (112 mg., 0.827 mmoles) and 1-cyclohexyl-3-(2-morpholinoethyl)-carbodiimide metho-p-toluene sulfonate (438 mg., 0.827 mmoles) were sequentially dissolved in 50 ml. of methylene chloride at 0° C. and the resulting solution stirred for 19 hours at 20° C. The reaction mixture was worked up as in step A to yield 555 mg. of a foam which was purified by chromatography (silica gel, 95:5 CH$_2$Cl$_2$/MeOH) to afford 136 mg. of purified product as a foam ($^1$H NMR, CDCl$_3$, 1.5 delta, 9H s [BOC]).

H. Title Compound

[N-(t-butyloxycarbonyl)-phenylalanine]-histidine-statine-(N-epsilon-benzyloxycarbonyl-lysine)-phenyl-alanine benzyl ester (136 mg., 0.17 mmole) and 70 mg. of 20% Pd(OH$_2$)/C catalyst were sequentially added to 15 ml. of methanol and the resulting mixture hydrogenated for four hours at 50 psi of H$_2$ and 20° C. The reaction mixture was then filtered through Super-Cel and evaporated to dryness to yield 76 mg. of a glass, which was triturated with ether to afford 63 mg. of purified [N-(t-butyloxycarbonyl)-phenylalanine]-histidine-statine-lysine-phenylalanine as a powder ($^1$NMR, CD$_3$OD, 1.5 delta, 9H s [BOC]).

EXAMPLE 2

[N-(t-butyloxycarbonyl)-Phe]-His-Sta-Ile-Sta (sodium Salt)

A. [N-(t-butyloxycarbonyl)-Isoleucine]-Statine Ethyl Ester

Statine ethyl ester hydrochloride (717 mg., 3 mmoles), N-methyl-morpholine (304 mg., 3 mmoles), N-(t-butyloxycarbonyl)-L-isoleucine ½H$_2$O (865 mg., 3.6 mmoles), N-hydroxybenzotriazole (486 mg., 3.6 mmoles) and 1-cyclohexyl-3-(2-morpholinoethyl)carbodiimide metho-p-toluene sulfonate (1.91 g., 80% pure, 3.6 mmoles) were added sequentially to 100 ml. of methylene chloride at 0° C. and the resulting solution allowed to stir for 19 hours at 20° C. The reaction mixture was then washed consecutively with 75 ml. of 5.5% aqueous HCl, 75 ml. of saturated aqueous NaHCO$_3$ and 75 ml. of brine, and dried over anhydrous MgSO$_4$. After filtration and evaporation, 1.39 g. of crude product was obtained as a foam ($^1$NMR, CDCl$_3$, 1.5 delta, 9H s [BOC]), which was used without further purification in the next step.

B. to G.
[N-(t-butyloxycarbonyl)-Phenylalanine]-Histidine-Statine-Isoleucine-Statine Ethyl Ester In like manner to that described in steps B to G of Example 1,[N-(t-butyloxycarbonyl)-isoleucine]-statine ethyl ester from step A (1.37 g.) was converted to purified title product (121 mg., foam, $^1$H NMR, CDCl$_3$, 1.5 delta, 9H s [BOC]). 95:5 CHCl$_3$/MeOH was used as the gradient in the chromatographic purification of step G.

H. Title Compound

A solution of [N-(t-butyloxycarbonyl)-phenylalanine]-histidine-statine-isoleucine-statine ethyl ester from step G (120 mg., 0.14 mmoles) in 2 ml. of dimethoxyethane was treated with 0.17 ml. of 1N aqueous NaOH. After 2.5 hours stirring at 20° C., another 0.17 ml. of 1N aqueous NaOH was added. After an additional two hours stirring, the reaction mixture was processed in a rotary evaporator to remove the dimethoxyethane, diluted with 5 ml. of H$_2$O and, after adjustment to pH 7.8, freeze-dried. The freeze-dried residue was slurried in ether. The supernatant was evaporated to dryness to yield 88 mg. of a foam, which on trituration with a small volume of ether afforded purified [N-(t-butyloxycarbonyl)-phenylalanine]-histidine-statine-isoleucine-statine (sodium salt) as a yellowish powder (65 mg., $^1$H NMR, CDCl$_3$, 1.5 delta, 9H s [BOC]).

EXAMPLE 3

[N-)t-butyloxycarbonyl)-Phe]-His-Sta-Ile-[Amino(n-butyric Acid)]

A. N-(t-butyloxycarbonyl)-Isoleucine]-[Amino(n-butyric Acid)]Benzyl Ester

N-(t-butyloxycarbonyl)-L-isoleucine (2.4 g., 10 mmoles), N-methyl-morpholine (1.0 g., 10 mmoles), benzyl 4-aminobutyrate hydrochloride (1.93 g., 10 mmoles), N-hydroxybenzotriazole (1.35 g., 10 mmoles) and 1-cyclohexyl-3-(2-morpholinoethyl)carbodiimide metho-p-toluene sulfonate (4.23 g., 80% pure, 10 mmoles) were sequentially dissolved in 60 ml. of methylene chloride at 0° C. and the resulting solution allowed to stir for 19 hours at 20° C. The reaction mixture was then evaporated to dryness and the residue dissolved in ethyl acetate. This solution was washed twice with 50 ml. of 5% aqueous HCl, twice with 50 ml. of 1N aqueous NaOH, once with H$_2$O and once with brine, dried over anhydrous MgSO$_4$, and filtered and concentrated in a rotary evaporator to 2.87 g. of crude product as a foam ($^1$H NMR, CDCl$_3$, 1.5 delta, 9H s [BOC]), which was used in the next step without further purification.

B. Isoleucine-[Amino(n-butyric Acid)]Benzyl Ester Hydrochloride

[N-(t-butyloxycarbonyl)-isoleucine]-[amino(n-butyric acid)]benzyl ester from step A (2.87 g., 7.1 mmoles) was dissolved in 10 ml. of 3.7N HCl/dioxane and the resulting solution allowed to stand for one hour at 20° C. The reaction solution was then evaporated to dryness to afford, after ether trituration, 2.4 g. of crude product as a white solid ($^1$H NMR, CD$_3$OD, 5.2 delta, 2H s [benzyl CH$_2$]), which was used without purification in the next step.

C. [N-(t-butyloxycarbonyl)-Statine]-Isoleucine[Amino(n-butyric Acid)]Benzyl Ester N-(t-butyloxycarbonyl)-statine (275.35 mg., 1 mmole), N-methyl-morpholine (101 mg., 1.0 mmole), isoleucine-[amino(n-butyric acid)]benzyl ester hydrochloride from step B (342 mg., 1 mmole), N-hydroxybenzotriazole (135 mg., 1.0 mmole) and dicyclohexylcarbodiimide (206 mg., 1.0 mmole) were sequentially added to 20 ml. of methylene chloride at 0° C., and the resulting solution was allowed to stir for 19 hours at 20° C. The reaction solution was then filtered and evaporated to a residue which was slurried in ethyl acetate. The slurry was filtered and the filtrate evaporated to dryness. After chromatography of the resulting residue (silica gel, CHCl$_3$/EtOAc gradient), 464 mg. of purified product was obtained ($^1$H NMR, CDCl$_3$, 1.5 delta, 9H s [BOC]).

D. Statine-Isoleucine-[Amino(n-butyric Acid)]Benzyl Ester Hydrochloride

In like manner to that described in step B, [N-(t-butyloxycarbonyl)-statine]-isoleucine-[amino(n-butyric acid)]benzyl ester from step C (464 mg., 0.82 mmole) was deblocked to yield 416 mg. of crude product as a white solid, which was used without purification in the next step ($^1$H NMR, CD$_3$OD, 5.2 delta, 2H s [benzyl CH$_2$]).

E. [N-alpha-(t-butyloxycarbonyl)-N-im-(t-butyloxy carbonyl)-Histidine]-Statine-Isoleucine[Amino(n-butyric acid)]Benzyl Ester In like manner to that described in step C, statine-isoleucine-[amino(n-butyric acid)]benzyl ester hydrochloride from step D (416 mg., 9.83 mmoles) was coupled with N-alpha-(t-butyloxycarbonyl)-N-im-(t-butyloxycarbonyl)-L-histidine (295 mg., 0.82 mmoles) to afford 391 mg. of purified product ($^1$H NMR, CDCl$_3$, 1.5 delta, 9H s [BOC]and 1.6 delta, 9H s [BOC]).

F. Histidine-Statine-Isoleucine-[Amino(n-butyric Acid)]Benzyl Ester Dihydrochloride In like manner to that described in step B, [N-alpha-(t-butyloxycarbonyl)-N-im(t-butyloxycarbonyl)-histidine [-statine-isoleucine-[amino(n-butyric acid)]benzyl ester from step E (391 mg., 0.49 mmoles) was deblocked to yield 328 mg. of crude product as a white solid ($^1$H NMR, CD$_3$OD, 5.2 delta, 2H s [benzyl CH$_2$]), which was used without purification in the next step.

G. [N-(t-butyloxycarbonyl)-Phenylalanine]-Histidine-Statine-Isoleucine-[Amino(n-butyric Acid]Benzyl Ester Histidine-statine-isoleucine-[amino(n-butyric acid)]-benzyl ester dihydrochloride from step F (328 mg., 0.487 mmoles), N-methyl-morpholine (0.128 ml., 1.17 mmoles), N-(t-butyloxycarbonyl)-L-phenylalanine (155 mg., 0.585 mmoles), N-hydroxybenzotriazole (79 mg., 0.585 mmoles) and dicyclohexylcarbodiimide (121 mg., 0.585 mmole) were sequentially dissolved in 20 ml. of methylene chloride at 0° C., and the resulting solution was stirred for 19 hours at 20° C. The reaction mixture was then worked up and chromatographed as in step C to afford 324 mg. of purified product ($^1$H NMR, CDCl$_3$, 1.5 delta, 9H s [BOC]).

H. Title Compound

A solution of [N-(t-butyloxycarbonyl)-phenylalanine]-histidine-statine-isoleucine-[amino(n-butyric acid)]benzyl ester from step G (324 mg., 0.38 mmoles) in 5 ml. of methanol was hydrogenated at room temperature and 50 psi of H$_2$ for one hour using a 20% Pd(OH)$_2$/C catalyst. The reaction mixture was then filtered to remove the catalyst and the supernatant evaporated to dryness. After trituration of the resulting residue with ether, 190 mg. of pure [N-(t-butyloxycarbonyl)-phenylalanine]-histidine-statine-isoleucine-[amino(n-butyric acid)]was obtained as a white powder ($^1$H NMR, CDCl$_3$, 1.5 delta, 9H s BOCl).

EXAMPLE 4

[N-(t-butyloxycarbonyl)-Phe]His-Sta[Amino(4-sec butyl-butyric Acid)]

A N-(t-butyloxycarbonyl)-Isoleucinal

A solution of N-(t-butyloxycarbonyl)-L-isoleucine methyl ester (10.0 g., 40.7 mmoles) in 100 ml. of toluene was cooled to −75° C. and then treated dropwise with 102 ml. of 1M diisobutylaluminum hydride in toluene such that the temperature of the reaction was maintained at less than −65° C. After the addition was complete, the reaction was stirred for ten minutes at −75° C. and then slowly quenched with 10 ml. of methanol while maintaining the temperature below −65° C. The reaction solution was then poured into 200 ml. of a cold saturated aqueous solution of Rochelle salt. The resulting mixture was overlayed with ether and stirred for one hour, after which the organic layer was separated, washed with brine, dried over anhydrous Na$_2$SO$_4$, filtered and evaporated to dryness to yield 7.0 g. of crude product ($^1$H NMR, CDCl$_3$, 1.5 delta, 9H s [BOC]), which was used in the next step without purification.

B. Ethyl L-(4-amino-4-sec butyl-butyrate) Hydrochloride

N-(t-butyloxycarbonyl)-isoleucinal from step A (1 g., 4.6 mmoles) and carbethoxymethylene triphenylphosphorane (1.93 g., 5.56 mmoles) were dissolved in 50 ml. of chloroform and the resulting solution allowed to stand for 48 hours at 20° C. The reaction mixture was then evaporated to dryness and purified by chromatography (silica gel, CHCl$_3$) to afford 1 g. of purified ethyl L-(4-(t-butyloxycarbonylamino)-4-sec butyl-delta-2-butyrate]as an oil ($^1$H NMR, CDCl$_3$, 4.2 delta, 2H s [ethyl CH$_2$]). The ethyl L-[4-(t-butyloxycarbonylamino) -4-sec butyl-delta-2-butyrate](300 mg., 1.05 mmoles) was then hydrogenated for about two hours at 50 psi of H$_2$ and 20° C. in methanol containing a 20% Pd(OH)$_2$/C catalyst. The reaction mixture was then filtered to remove the catalyst and the filtrate was concentrated in a rotary evaporator to yield 300 mg. of crude ethyl L-[4-(t-butyloxycarbonylamino)-4-sec butyl-butyrate]as an oil ($^1$H NMR, CDCl$_3$, 4.2 delta, 2H s, [ethyl CH$_2$]). The ethyl L-[4-(t-butyloxycarbonylamino) -4-sec butyl-butyrate](300 mg.) was then dissolved in 4 ml. of 3.7N HCl/dioxane and the resulting solution stirred for one hour at 20° C. The reaction mixture was then evaporated to dryness to afford 231 mg. of crude product as a foam, which was used without purification in the next step ($^1$H NMR, CDCl$_3$, 4.2 delta, 2H s [ethyl CH$_2$]).

C. [N-(t-butyloxycarbonyl)-Statine]-[Amino(4-sec butyl-butyric Acid)]Ethyl Ester N-(t-butyloxycarbonyl)-statine (286 mg., 1.04 mmoles), ethyl L-(4-amino-4-sec butyl-butyrate) hydrochloride from step B (232 mg., 1.04 mmoles), N-hydroxybenzotriazole (141 mg., 1.04 mmoles), N-methylmorpholine (105 mg., 1.04 mmoles and dicyclohexyl carbodiimide (215 mg., 1.04 mmoles) were sequentially added to 15 ml. of methylene chloride at 0° C., and the resulting solution was stirred for 19 hours at 20° C. The reaction mixture was then filtered and the supernatant evaporated to dryness. Chromatography of this residue (silica gel, CHCl$_3$/EtOAc gradient) afforded 400 mg. of purified product ($^1$H NMR, CDCl$_3$, 1.5 delta, 9H s [BOC]).

D. to G. [N-(t-butyloxycarbonyl)-Phenylalanine]-Histidine -Statine-[Amino(4-sec butyl-butyric Acid)]Ethyl Ester In like manner to that described in steps D to G of Example 3, [N-(t-butyloxycarbonyl)-statine]-[Amino(4-sec butyl-butyric acid)]ethyl ester from step C (400 mg., 0.94 mmoles) was converted to purified [N-(t-butyloxycarbonyl)-phenylalanine]-histidine-statine -[amino(4-sec butyl-butyric acid)]ethyl ester (211 mg., $^1$H NMR, CDCl$_3$, 1.5 delta, 9H s [BOC]).

H. Title Compound

A solution of [N-(t-butyloxycarbonyl)-phenylalanine]-histidine-statine-[amino(4-sec butyl-butyric acid)]ethyl ester from step G (200 mg., 0.274 mmoles) in 5 ml. of dimethoxyethane was treated with 0.3 ml. of 1N aqueous NaOH, and the resulting mixture was stirred for three hours at 20° C. Another 0.3 ml of 1N aqueous NaOH was then added and the reaction mixture stirred for an additional hour at 20° C. The reaction mixture was then concentrated in a rotary evaporator to remove the dimethoxyethane, treated with ethyl acetate and then adjusted to pH 2 with 5% aqueous HCl. The organic layer was separated, washed with brine, filtered, dried over anhydrous MgSO$_4$ and concentrated to a white solid, which on trituration with ether afforded 35 mg. of purified [N-(t-butyloxycarbonyl)-phenylalanine]-histidine -statine-[amino(4-sec butyl-butyric acid)](¹H NMR, CDCl$_3$, 1.5 delta, 9H s [BOC]).

EXAMPLE 5

[N-(t-butyloxycarbonyl)-Phe]-His-Aminostatine-Ile-Phe Diacetate

A. Ethyl 4(S)-(t-butyloxycarbonylamino)-3-(S)-azido6-methyl-heptanoate and Ethyl 4(S)-(t-butyloxycarbonylamino) -6-methyl-trans-2-heptenoate A mixture of 3-epi-N-(t-butyloxycarbonyl)-statine (7.6 g., 25.05 mmoles) and triethylamine (2.78 g., 27.55 mmoles) in methylene chloride (200 ml.) was treated at 0° C. with 3.15 g. (27.55 mmoles) of methanesulfonyl chloride added dropwise. The resulting mixture was stirred for one hour at 0° C., allowed to warm to room temperature over the course of one hour and then washed with 1N aqueous HCl solution (2 ×200 ml.) and saturated aqueous NaHCO$_3$ solution (1 × 200 ml.). The organic layer was dried over MgSO$_4$ and evaporated to yield 9.75 g. of a yellow oil. A solution of this oil in N,N-dimethylformamide (150 ml.) was treated with sodium azide (2.45 g., 37.7 mmoles) and the resulting mixture was heated for four hours at 60° C. The solvent was then removed under high vacuum and the residue diluted with 500 ml. of H$_2$O and extracted with ether (2 × 150 ml.). The combined ether extract was washed with brine (1 × 100 ml.), dried (MgSO$_4$) and evaporated to afford 6.6 g. of a light yellow oil. Separation of the oil by flash chromatography using 25-30% ether in hexane as eluant gave 334 mg. (4% yield) of ethyl 4(S)-(t-butyloxycarbonylamino) -(S)-azido-6-methylheptanoate as an oil [R$_f$=0.62 in ether-hexane, 1:1; ¹H-NMR (CDCl$_3$): delta 0.95 (d, J=6,6H), 1.30 (t, J=7, 3H), 1.47 (s, 9H), 2.58 (d, J=7, 2H), 4.17 (q, J=7, 2H), 4.53 (broad d, 1H); ¹³C-NMR (CDCl$_3$) delta 14.2, 22.2, 23.0, 24.9, 28.4, 37.2, 42.4, 51.6, 61.1, 62.8, 79.6, 155.8, 171.0; IR (CHCl$_3$) 3473, 2102 cm$^{-1}$]and, in the more polar chromatographic fraction, 4.9 g. of a clear oil (R$_f$=0.55 in etherhexane, 1:1) which crystallized upon standing. Trituration in ice cold hexane gave 3.78 g. (53% yield) of ethyl 4(S)-(t-butyloxycarbonylamino)-6-methyltrans-2-heptenoate as a fluffy white solid [mp 56-58° C.; ¹H-NMR (CDCl$_3$ ): delta 0.93 (d, J=6,6H), 1.30 (t, J=7, 3H), 1.47 (s, 9H), 4.18 (q, J=7,2H), 5.9 (dd, J=15,1,1H), 6.83 (dd, J=15,5,1H); IR (KBr): 3350, 3307, 1720, 1701, 1684, 1659 cm-¹]. amino)-3,4(S,S)-6-methylheptanoate from Ethyl (4S)-t-butyloxycarbonylamino Butyloxycarbonylamino-6-methyl-trans-2-heptenoate A mixture of ethyl 4(S)-(t-butyloxycarbonylamino) -6-methyl-trans-2-heptenoate (3.52 g., 12.35 mmoles), benzylamine (3.97 g., 37.0 mmoles) and abs. EtOH (90 ml.) was heated for 7 days at 58° C. The reaction mixture was then evaporated and separated by flash chromatography using 10-15% ethyl acetate in hexane as eluant. The less polar fractions gave 963 mg. (20% yield) of product as an oil [R$_f$=0.32 in 25% EtOAc in hexane; ¹H-NMR (CDCl$_3$): delta 0.97 (d, J=5, 6H), 1.25 (t, 3H, J=7), 1.45 (s, 9H), 2.43 (m, 2H), 3.32 d (m, 1H), 3.77 (s, 2H), 4.10 (q, 2H, J=7), 4.65 (d, 1H, J=9), 7.22 (s, 5H); IR (CHC13) 3433, 1720 (shoulder), 1709 cm$^{-1}$; Mass spectrum m/e 393 (M+ +1), 319, 206 (base), 91].

B(2). Ethyl 3-Benzylamino-4-(t-butyloxycarbonylamino) -3,4(S,S)-6-methylheptanoate from Ethyl 4(S)-(t-Butyloxycarbonylamino) -3(S)-azido-6-methylheptanoate 20 mg. of 10% Pd/C catalyst was added to a solution of ethyl 4(S)-(t-butyloxycarbonylamino)-3(S)-azido -6-methylheptanoate (120 mg., 0.36 mmole) in 5 ml. of acetic acid: ethanol, 1:1, and the resulting mixture hydrogenated for three hours at room temperature and 1 atm. H$_2$. After removal of the catalyst by filtration, the reaction mixture was evaporated to a residual oil under reduced pressure using an ethanol azeotrope. This oil (136 mg.) was then dissolved in 3 ml. of methanol and treated sequentially with 37 microliters (38.2 mg., 0.36 mmoles) of benzaldehyde at room temperature and 34 mg. (54 mmoles) of NaCNBH$_3$ at 0° C. The reaction mixture was stirred for 0.5 hr. at 0° C. and then was allowed to warm to room temperature before being diluted with H$_2$O and saturated aqueous NaHCO$_3$ solution. An oily precipitate formed, which was extracted with methylene chloride. The resulting organic layer was dried (MgSO$_4$) and evaporated to an oily residue. TLC of the oily residue showed only one epimer corresponding to ethyl 3-benzylamino-4-(t-butyloxycarbonylamino) -3-4(S,S)-6-methylheptanoate. Purification of said oily residue by flash chromatography using 10-15% ethyl acetate:hexane yielded 68 mg. of product, which was identical by NMR and TLC to the material prepared in step B(1).

C. 3-Benzyloxycarbonylamino-4-(t-butyloxycarbonylamino -3,4(S,S)-6-methylheptanoic Acid 60 mg. of 10% Pd/C catalyst was added to a solution of ethyl 3-benzylamino-4-(t-butyloxycarbonylamino) -3,4(S,S)-6-methylheptanoate from step B(1) (530 mg., 1.35 mmoles) in 12 ml. acetic acid: ethanol 1:1 and the resulting mixture hydrogenated for 3 hours at room temperature and 50 psi H$_2$. The catalyst was removed by filtration and the filtrate was concentrated to an oil which was taken up in a mixture of 10 ml. dioxane and 10 ml. H$_2$O. Solid NaHCO$_3$ was added to the reaction mixture (pH 7.8) followed by 289 microliters (345 mg., 2.025 mmoles) of benzyloxycarbonyl chloride (Chemalog). The resulting mixture was stirred for 1.5 hours at room temperature while maintaining the pH at 8 with solid NaHCO$_3$. Then, the mixture was stirred for an additional 4 hours at pH 12.5 by adding 4 ml. of aqueous 1N NaOH solution and H$_2$O -dioxane when necessary to dissolve any precipitate. The mixture was then neutralized with 1N aqueous HCl at 0° C. and the dioxane removed under reduced pressure. The residue was diluted with 50 ml. of H$_2$O and extracted with ethyl acetate (2×50 ml.). The combined ethyl acetate extract was dried (MgSO$_4$) and evaporated to yield 588 mg. of an oil, which was purified by flash chromatography using 3% MeOH in CHCl$_3$ as eluent to give 288 mg. (41% yield) of product as an oil [¹H-NMR (DMSO d$_6$, 250 MHz): delta 0.81 (d, J=7, 3H), 0.86 (d, J=7, 3H), 1.38 (s, 9H), 2.2-2.4 (m, 2H), 5.02 (centroid of AB pattern, J=13, 2H), 6.48 (d, J=9, 1H), 7.05 (d, J=9,1H), 7.30 (s, 9H); Mass spectrum: m/e 186, 130, 91, 86 (Base)].

D. Isoleucine-Phenylalanine Benzyl Ester Hydrochloride

A solution of 14.05 g. (58.5 mmoles) of N-(t-butyloxycarbonyl) -L-isoleucine hemihydrate (Chemalog) in 500 ml. of methylene chloride was dried (MgSO$_4$), filtered and treated with 6.43 ml. (5.92 g., 58.5 mmoles) of N-methyl-morpholine. The resulting mixture was chilled to −16° C. and then treated with 7.59 ml. (7.99 g., 58.5 mmoles) of isobutylchloroformate at such a rate that the temperature of the exothermic reaction did not exceed −10° C. After 10 minutes of additional stirring following completion of this addition, a solution of 24.8 g. (58.0 mmoles) of L-phenylalanine benzyl ester p-toluenesulfonate and 6.43 ml. (5.92 g., 58.5 mmoles) of N-methyl-morpholine in 50 ml. of methylene chloride was added dropwise to the reaction mixture at such a rate that the temperature of the exothermic reaction did not exceed −10° C. When this addition was complete, the reaction mixture was allowed to warm to room temperature over the course of an hour, and was then washed with 5% aqueous HCl solution (2 ×300 ml.) and 10% aqueous K$_2$CO$_3$ solution (2 ×300 ml.). The resulting organic layer was dried (MgSO$_4$) and evaporated to afford 27.40 g. of a white solid. Trituration in hexane gave 24.97 g. of purified [N-(t-butyloxycarbonyl) -L-isoleucine]-L-phenylalanine benzyl ester [42% yield; m.p. 131–132° C., R$_f$=0.43 in ether:ethyl acetate,1:1; $^1$H-NMR (CDCl$_3$) delta: 0.78–0.9 (broad d, 6H), 1.43 (s, 9H), 3.08 (d, J=6), 3.87 (dd, J=5, 9, 1H), 4.75–5.1 (m, 1H), 5.06 (s, 2H), 6.3 (d, J=9, 1H), 7.0–7.3 (m, 11H)]. A solution of 12.50 g. (25.7 mmoles) of [N-(t-butyloxycarbonyl)-L-isoleucine]-Lphenylalanine benzyl ester in 125 ml. of 4N HCl in dioxane was stirred for 2 hours at room temperature while protected from atmospheric moisture with a CaCl$_2$ tube. The solvent was then removed under reduced pressure and the residue triturated in ether to afford 11.16 g. of product as a white solid [m.p. 178–179° C.] (dec); R$_f$=0.73 in BuOH-H$_2$-AcOH, 4:1:1; ($^1$H-NMR (CD$_3$OD) delta: 0.9-1.1 (m, 6H), 3.1-3.0 (m, 2H), 3.73 (d, J=5, 1H), 5.08 (s, 1H), 7.18 (s, 5H), 7.24 (s, 5H).

E. [N-Gamma-(t-butyloxycarbonyl)-Benzyloxycarbonylaminostatine]-Isoleucine-Phenylalanine Benzyl Ester A solution of isoleucine-phenylalanine benzyl ester hydrochloride (412 mg., 1.02 mmoles) in 10 ml. of methylene chloride was neutralized at 0° C. with 142 microliters of triethylamine (103 mg., 1.02 mmoles). 3-benzyloxy-carbonylamino-4-(t-butyloxycarbonylamino)-3,4(S,S)-6-methylheptanoic acid (416 mg., 1.02 mmoles) and N-hydroxybenzotriazole (205 mg., 1.52 mmoles) were then added to the solution at 0° C. Finally, a solution of dicyclohexylcarbodiimide (210 mg., 1.02 mmoles) in 5 ml. of methylene chloride was added at 0° C. The reaction mixture was then stirred for 3 hours at 0° C. and for an additional 16 hours with warming to room temperature. The solvent was then removed under reduced pressure and the residue stirred in 75 ml. of ethyl acetate. The resulting mixture was filtered to remove a quantity of solids and the filtrate washed with 10% aqueous citric acid (1 ×75 ml.) and saturated aqueous NaHCO$_3$ solution (1 ×75 ml.), dried (MgSO$_4$) and evaporated to a solid (217 mg.). This solid was combined with the solids that were filtered from the ethyl acetate mixture (see preceding sentence). The combined solids (1.043 g.), a mixture of product and dicyclohexylurea, were used in the next step without purification.

F. Benzyloxycarbonylaminostatine-Isoleucine-Phenylalanine Benzyl Ester Hydrochloride The crude [N-gamma-(t-butyloxycarbonyl)benzyloxycarbonylaminostatine]-isoleucine-phenylalanine benzyl ester from step E (1.043 g.) was stirred in 25 ml. of 4N HCl in dioxane for one hour at room temperature while protected from atmospheric moisture with a CaCl2 tube. Removal of the solvent under reduced pressure (using a methylene chloride and ether azeotrope) and trituration in ether gave 963 mg. of a crude solid, which was a mixture of product and dicyclohexylurea. This crude solid was used in the next step without purification.

G. [N-Alpha-(t-butyloxycarbonyl)-N-im-(t-butyloxycarbonyl) -Histidine]-BenzyloxycarbonylaminostatineIsoleucine -Phenylalanine Benzyl Ester A suspension of the crude benzyloxycarbonylamino -statine-isoleucine-phenylalanine benzyl ester hydrochloride from step F (963 mg.) in 20 ml. of methylene chloride was neutralized at 0° C. with 177 microliters of triethylamine (128 mg., 1.02 mmoles). N-Alpha-(t-butyloxycarboneyl) -N-im-(t-butyloxycarbonyl)-L-histidine (542 mg., 1.53 mmoles) and N-hydroxybenzotriazole (206 mg., 1.53 mmoles) were then added to the suspension at 0° C. Finally, a solution of dicyclohexylcarbodiimide (315 mg., 1.53 mmoles) in 1 ml. of methylene chloride was added at 0° C. The reaction mixture was then stirred for 3 hours at 0° C. and for an additional 16 hours at room temperature. About one-half of the solvent was removed under reduced pressure and the residue stirred in 125 ml. of ethyl acetate. The resulting mixture was filtered to remove a quantity of solids and the filtrate washed with aqueous 10% citric acid solution (2 ×100 ml.) and aqueous saturated NaHCO$_3$ solution (1 ×100 ml.), dried (MgSO$_4$) and evaporated to 920 mg. of a solid. This solid was purified by flash chromatography using 0.5%–0.75% MeOH in CHCl$_3$ as eluent to provide 221 mg. of purified product as a solid. The solids that were filtered from the ethyl acetate mixture (see two sentences above) contained a substantial amount of product along with dicyclohexylurea. Most of the dicyclohexylurea in said solids was separated from the product by filtration after trituration of the solids (with vigorous stirring) in 100 ml. of methylene chloride. The filtrate was concentrated (1.1 g.) and chromatographed identically as above to provide an additional 401 mg. of product. The combined purified solid products were triturated in ether to afford 592 mg. of a flaky white solid [58% yield; m.p. 229°–231° C.; R$_f$=0.22 in 2.5% MeOh in CHCl$_3$; $^1$H-NMR (CDCl$_3$, 250 MHz): delta 0.6–0.85 (m, 12H), 1.42 (s, 9H), 1.58 (s, 9H), 2.42 (centroid of AB pattern of ABX, 2H, J$_{AB}$=14, J$_{AX}$=5, J$_{BX}$=10), 2.94 (d, J=5, 2H), 3.13 (d, J=6, 2H), 3.55-3.7 (m, 1H), 4.1–4.3 (m, 3H), 4.98 (q, J=7, 1H), 5.2–5.5 (m, 4H), 6.10 (d, J=7, 1H), 6.37 (broad d, 1H), 6.80 (d, 1H, J=8), 7.0-7.4 (m, 17H), 7.5 (broad, 1H), 8.00 (s, 1H)].

H. Histidine-Benzyloxycarbonylaminostatine-Isoleucine-Phenylalanine Benzyl Ester Hydrochloride A solution of 204 mg. of [N-alpha-(t-butyloxycarbonyl) -N-im-(t-butyloxycarbonyl)-histidine]-benzyloxycarbonylaminostatine-isoleucine-phenylalanine benzyl ester in 7 ml. of 4N HCl in dioxane was stirred for 5 hours at room temperature while protected from atmospheric moisture with a CaCl$_2$ tube. The solvent was removed under reduced pressure (using a methylene chloride and ether azeotrope) to afford 153 mg. of product as a white powder [86% yield; m.p. 154–157° C.; R$_f$=0.55 in butyl alcohol:H$_2$O: acetic acid (4:1:1); $^1$H-NMR (CD$_3$OD): delta 1.05-1.1 (m, 12H), 2.3-2.5 (m, 2H), 3.1 (d, J=8, 2H), 5.08 (s, 4H), 7.18 (s, 5H), 7.30 (s, 10H), 7.53 (s, 1H), 8.83 (s, 1H)].

I. [N-(t-butyloxycarbonyl)-Phenylalanine]-Histidine-Benzyloxycarbonylaminostatine-Isoleucine-Phenylalanine Benzyl Ester A solution of histidine-benzyloxycarbonylamino -statine-isoleucine-phenylalanine benzyl ester hydrochloride (306 mg., 0.352 mmoles) in 5 ml. of dimethylformamide was neutralized at 0° C. with 123 microliters of triethylamine (88 mg., 0.879 mmoles). N-(t-butyloxycarbonyl) -L-phenylalanine (103 mg., 0.387 mmoles) and N-hydroxybenzotriazole (79 mg., 0.580 mmoles) were then added to the solution at 0° C. Finally a solution of dicyclohexylcarbodiimide (980 mg., 0.387 mmoles) in 1.5 ml. of dimethylformamide was added at 0° C. The reaction mixture was then stirred for 3 hours at 0° C. and for an additional 16 hours at room temperature. The solvent was removed under high vacuum, the residue was stirred in 50 ml. of ethyl acetate and the resulting mixture was filtered to remove a quantity of solids. The solvent was removed from the filtrate, the residue was stirred in methylene chloride (50 ml.) and the resulting mixture was filtered to remove a second quantity of solids. The filtrate from the second filtration was concentrated, the residue dissolved in 50 ml. of ethyl acetate and the resulting solution washed with 10% aqueous citric acid (2×40 ml.) and saturated aqueous NaHCO$_3$ solution (2×40 ml.). The resulting organic layer was dried (MgSO$_4$) and concentrated to a solid (153 mg.). This solid and the solids from the ethyl acetate and methylene chloride triturations were combined and purified by flash chromatography, using 2–3% methanol in chloroform as eluent, to give 261 mg. of a solid. Trituration of this solid in ether afforded 218 mg. of product as a glassy solid [59% yield; m.p. 228°–229° C.; R$_f$=0.25 in 5% MeOH in chloroform; $^1$H-NMR (CDCl$_3$, 250 MHz ) : delta 0.6–0.8 (m, 12H), 1.26 (s, 9H), 2.38 (broad d, 2H), 2.8–3.0 (m, 2H), 3.15–3.4 (m, 4H), 4.1–4.0 (m, 1H), 4.1–4.2 (m, 1H), 4.2–4.4 (m, 2H), 4.6 (broad d, 1H), 4.9–5.2 (m, 6H), 5.9–6.1 (m, 1H), 6.78 (s, 1H), 7.2–7.4 (m, 22H), 7.49 (s, 1H)].

J. Title Compound

10% Pd/C catalyst (12 mg.) was added to a solution of [N-(t-butyloxycarbonyl)-phenylalanine]-histidine-benzyloxycarbonylaminostatine -isoleucine-phenylalanine benzyl ester (24 mg., 0.023 mmoles) in 5 ml. of acetic acid:ethanol (1:1), and the resulting mixture hydrogenated for 3 hours at room temperature and 40 psi H$_2$. The reaction mixture was then filtered to remove the catalyst and the filtrate concentrated to a residue. Trituration of the residue in ether afforded 17 mg. of [N-(t-butyloxycarbonyl)-phenylalanine]-histidine-amino-statine -isoleucine-phenylalanine diacetate as a white powder [m.p. 155°–159° C.; R$_f$=0.58 in n-butyl alcohol; H$_2$O; acetic acid (4:1:1); $^1$H-NMR (CD$_3$CO$_2$D 250 MHz): delta 0.7–1.0 (m, 12H), 1.33 (s, 9H), 2.7–2.9 (m, 2H), 3.0–3.6 (m, 6H), 3.6–3.9 (m, 1H), 4.15–4.30 (m, 1H), 4.35–4.55 (m, 2H), 4.8–4.95 (m, 2H), 7.1–7.4 (m, 10H), 7.38 (s, 1H), 8.78 (s, 1H)].

EXAMPLE 6

[N-(t-butyloxycarbonyl)-Phe]-His-Sta-Ala-Sta-Glu Dibenzyl Ester

A. [N-(t-butyloxycarbonyl)-Alanine]-Statine- Glutamic Acid Dibenzyl Ester

A. [N-(t-butyloxycarbonyl)-Alanine]-Statine-Glutamic Acid Dibenzyl Ester

N-hydroxybenzotriazole (324 mg., 2.4 mmoles), N-methyl-morpholine (202 mg., 2 mmoles), L-glutamic acid dibenzyl ester p-toluenesulfonate (995 mg., 2 mmoles), N-(t-butyloxycarbonyl)-statine (660 mg., 2.4 mmoles) and 1-cyclohexyl-3-(2-morpholinoethyl)carbodiimide metho p-toluene sulfonate (1271 mg., 80% pure, 2.4 mmoles) were sequentially dissolved in methylene chloride (100 ml.) at 0° C. and the resulting solution stirred for 19 hours at 20° C. The reaction mixture was then washed consecutively with 5.5% aqueous HCl, saturated aqueous NaHCO$_3$ solution and brine, and dried over anhydrous MgSO$_4$ After filtration and evaporation, 1269 g. of crude [N-(t-butyloxycarbonyl)-statine]-glutamic acid dibenzyl ester was obtained as an oil ($^1$H NMR, CDCl$_3$, 5.2 delta, 2H s [benzyl CH$_2$]). This oil (1269 g.) was dissolved in 10 ml. of 3.7N HCl/dioxane and the resulting solution allowed to stand for one hour at room temperature. The solution was then evaporated under high vacuum to a residue, which was triturated in ether and dried with nitrogen to yield 900 mg. of statine-glutamic acid dibenzyl ester hydrochloride as a foam ($^1$H NMR, CDCl$_3$, 5.2 delta, 2H s [benzyl CH$_2$]). N-hydroxybenzotriazole (186 mg., 1.38 mmoles), N-methyl-morpholine (116 mg., 1.15 mmoles), a quantity of the statine-glutamic acid dibenzyl ester hydrochloride foam formed above (600 mg., 1.15 mmoles), N-(t-butyloxycarbonyl)-L-alanine (261 mg., 1.38 mmoles) and 1-cyclohexyl-3-(2-morpholinoethyl)-carbodiimide metho p-toluene sulfonate (732 mg., 80% pure, 1.38 mmoles) were sequentially dissolved in methylene chloride (60 ml.) at 0° C. and the resulting solution stirred for 19 hours at 20° C. The reaction mixture was then washed consecutively with 5.5% aqueous HCl, saturated aqueous NaHCO$_3$ solution and brine, and dried over anhydrous MgSO$_4$ After filtration and evaporation, 743 mg. of crude product was obtained as a foam ($^1$H NMR, CDCl$_3$, 5.2 delta, 2H s [benzyl CH$_2$]).

B. to G. Title Compound

In like manner to that described in steps B to G of Example 1, [N-(t-butyloxycarbonyl)-alanine]-statine-glutamic acid dibenzyl ester from step A (743 mg.) was converted to [N-(t-butyloxycarbonyl)-phenylalanine]-histidine-statine-alanine-statine-glutamic acid dibenzyl ester (300 mg., foam, $^1$H NMR, CDCl$_3$, 5.2 delta, 2H s [benzyl CH$_2$]). In each deblocking step evaporation to dryness was followed by a trituration with ether. At the end of step E, the crude product foam was purified by chromatography (silica gel, 95:5 CHCl$_3$/methanol) to yield a purified foam. No chromatographic purification was performed at the end of step G.

EXAMPLE 7

[N-(t-butyloxycarbonyl)-Phe]-His-Sta-Ala-Sta-Glu

A mixture of [N-(t-butyloxycarbonyl)-phenylalanine]-histidine-statine-alanine-statine-glutamic acid dibenzyl ester (90 mg., 0.077 mmoles), 20% Pd(OH)$_2$/C catalyst(45 mg.) and methanol (10 ml.) was hydrogenated for 2 hours at room temperature and 50 psi H$_2$. The reaction mixture was then filtered to remove the catalyst and the filtrate evaporated to yield a foam (72 mg.). This foam was triturated with ether and dried to yield a purified [N-(t-butyloxycarbonyl)-phenylalanine]-histidine-statine-glutamic acid foam (51 mg., 72% yield, $^1$H NMR, CDCl$_3$, 1.5 delta, 9H s [BOC]).

EXAMPLE 8

[N-(t-butyloxycarbonyl)-Phe]-His-Sta-[Amino(2-sec butyl-ethylene)]-Phe Acetic Acid Salt A. N-(t-butyloxycarbonyl)-L-Isoleucinal A mixture of L-isoleucine methyl ester (24.3 g., 0.134 mmoles) and triethylamine (13.5 g., 0.134 mmoles) in methylene chloride (210 ml.) was prepared and a solution of ditertbutyldicarbonate (Aldrich, 29.1 g., 0.134 mmoles) in methylene chloride (25 ml.) was added dropwise to this mixture at 0° C. After completion of this addition, the mixture was allowed to warm to room temperature overnight and was then filtered. The filtrate was washed successively with H$_2$O (3×75 ml.), aqueous 0.1N HCl solution, H$_2$O (1×100 ml.) and saturated aqueous NaHCO$_3$ solution (1×75 ml.), dried (MgSO$_4$) and evaporated to yield N-(t-butyloxycarbonyl)-L-isoleucine methyl ester as an oil [30.7 g; 93% yield; $^1$H-NMR (CDCl$_3$): delta 0.92 (d, J=7, 6H), 1.43 (s, 9H), 3.70 (s, 3H), 4.17 (dd, J=5, 9, 1H), 5.03 (d, J=9, 1H)]. A solution of the N-(t-butyloxycarbonyl)-L-isoleucine methyl ester oil (15.0 g., 61.1 mmoles) in dry toluene (260 ml.) was cooled to −78° C., and a 1M solution of diisobutyl aluminum hydride in hexane (153 ml.) was added dropwise thereto at such a rate that the temperature of the exothermic reaction did not exceed −65° C. Followed by 15 minutes of additional stirring at −78° C. After completion of this addition, the mixture was carefully quenched with 15 ml. of methanol (the mixture temperature was not allowed to exceed −65° C.) followed by 200 ml. of Rochelle salt solution. After warming to room temperature, the organic layer was separated and extracted with ether (3×200 ml.); additional Rochelle salt solution was added when necessary to dissolve the aluminum salts. The combined organic extract was dried (Na$_2$SO$_4$) and evaporated to afford a crude product as an oil. The oil was stored at −78° C. to avoid possible racemization and was used without purification in the next step [132 g.; 98% yield; R$_f$=0.32 in 35% ether in hexane; $^1$H-NMR (CDCl$_3$) delta 1.00 (d, J=7, 6H), 1.46 (s, 9H), 9.65 (s, 1H)].

[Amino(2-sec butyl-ethylene)]-Phenylalanine Benzyl Ester Dihydrochloride

A mixture of N-(t-butyloxycarbonyl)-L-isoleucinal (2.00 g., 9.29 mmoles) and L-phenylalanine benzyl ester p-tosylate (Chemalog, 3.78 g., 8.84 mmoles) in methanol (150 ml.) was stirred for 35 minutes in the presence of 3 Angstrom molecular sieves (Ventron) at room temperature. 0.73 g. (11.6 mmoles) of NaCNBH$_3$ was then added and the mixture was stirred for another one hour at room temperature. The sieves were then filtered off and the filtrate concentrated to an oily residue, which was diluted with saturated aqueous NaHCO$_3$ solution and extracted twice with ether. The combined ether extract was dried (Na$_2$SO$_4$) and concentrated to an oil which was purified by flash chromatography using 12% ethyl acetate in hexane as eluent to afford 1.69 g. of [(t-butyloxycarbonyl)amino(2-sec buty-ethylene)]-phenylalanine benzyl ester as an oil (40% yield; R$_f$=0.28 in 25% ethyl acetate in hexane). The oil crystallized upon standing [m.p. 53–55° C.; $^1$H-NMR (CDCl$_3$) delta 0.6–1.0 (m, 6H), 1.48 (s, 9H), 2.92 (d, J=7, 2H), 5.07 (s, 2H), 7.17 (s, 5H), 7.25 (s, 5H)]. A solution of [(t-butyloxycarbonyl)amino(2-sec butylethylene)]-phenylalanine benzyl ester (2.94 g., 6.47 mmoles) in 4N HCl/ dioxane (110 ml.) was formed and stirred for 2 hours at room temperature, protected from the atmosphere with a CaCl$_2$ tube. The solvent was then removed under reduced pressure with an ether azeotrope and the residue was triturated with ether to afford a white solid [2.65 g.; 95% deblocking yield; m.p. 183°–184° C.; R$_f$=0.73 in BuOH: H$_2$O: acetic acid (4:1:1); $^1$H-NMR (CD$_3$OD): delta 1.00(broad d, 6H), 5.13 (s,2H), 7.1–7.5 (m, 10H)].

C. [N-(t-butyloxycarbonyl)-Statine]-[Amino(2-sec butyl-ethylene)]-(N-benzyloxycarbonyl-Phenylalanine) Benzyl Ester A suspension of [amino(2-sec butyl-ethylene)]-phenylalanine benzyl ester dihydrochloride (1.55 g., 3.63 mmoles) in methylene chloride (40 ml.) was chilled to 0° C. and neutralized at that temperature with triethylamine (0.808 g., 7.99 mmoles). N-(t-butyloxycarbonyl) -statine (1.00 g., 3.63 mmoles) and N-hydroxybenzotriazole (0.74 g., 5.45 mmoles) were then added to the suspension at 0° C. Finally, dicyclohexylcarbodiimide (0.75 g., 3.63 mmoles) in methylene chloride (2 ml.) was added to the suspension at 0° C. and the resulting mixture was stirred for 3 hours at 0° C. and then for another 16 hours at room temperature. A precipitate which had formed was then filtered off and the filtrate was concentrated and stirred in 125 ml. of ethyl acetate. After filtering off undissolved solids again, the ethyl acetate layer was washed with saturated aqueous NaHCO$_3$ solution (135 ml.), dried (Na$_2$SO$_4$) and evaporated to a foam. The foam was purified by flash chromatography using 35% ethyl acetate in hexane as eluent to afford a purified [N-(t-butyloxycarbonyl)-statine]-[amino(2-sec butylethylene)]-phenylalanine benzyl ester product as a foam [1.96 g.; 88% yield; Rf=0.58 in ethyl acetate: hexne, 1:1); $^1$H-NMR (CDCl$_3$) delta 0.6–1.1 (m, 12H), 1.5 (s, 9H), 4.88 (d, J=9, 1H), 5.06 (s, 2H), 7.15 (s, 5H), 7.25 (s, 5H)]. A solution of this purified [N-(t-butyloxycarbonyl)-statine]-[amino(2-sec butylethylene)]-phenylalanine benzyl ester foam (1.91 g., 3.12 mmoles) in dioxane (16 ml.) was acylated with benzyloxycarbonyl chloride (Chemalog, 67 microliters, 0.80 g., 4.68 mmoles) using saturated aqueous NaHCO$_3$ solution to maintain the pH at 8. When all the starting material was consumed (as indicated by TLC), the dioxane was removed under reduced pressure and the residue was diluted with H$_2$O and extracted with ethyl acetate. The ethyl acetate extract was dried (MgSO$_4$) and evaporated to a foam which was purified by flash chromatography to yield a white foam [2.06 g.; R$_f$=0.7 in ethyl acetate:hexane, (1:1); $^1$H-NMR (CDCl$_3$): delta 0.6–1.0 (m, 12H), 1.48 (s, 9H), 7.0–7.4 (m, 15H)].

D. to G.
[N-(t-butyloxycarbonyl)-Phenylalanine]-Histidine-Statine-[Amino(2-sec butyl-ethylene)][N-benzyloxycarbonyl-Phenylalanine]-Benzyl Ester In like manner to that described in steps F to I of Example 5, the purified [N-(t-butyloxycarbonyl)-statine]-[amino(2-sec butyl-ethylene)]-(N-benzyloxycarbonyl -phenylalanine) benzyl ester from step C (2.03 g., 2.72 mmoles) was converted to purified [N-(t-butyloxycarbonyl) -phenylalanine]-histidine-statine [amino(2-sec butyl-ethylene)]-(N-benzyloxycarbonylphenylalanine) benzyl ester [0.595 g.; foam; $R_f=0.36$ in 5% methanol in chloroform; 3 $^1$H-NMR (CDCl$_3$): delta 0.6–1.0 (m, 12H), 1.38 (s, 9H), 6.75 (s, 1H), 7.1–7.3 (m, 20H), 7.38 (s, 1H)].

H. Title Compound

10% Pd/C catalyst (18 mg.) was added to a solution of [N-(t-butyloxycarbonyl)-phenylalanine]-histidine-statine [amino(2-sec butyl-ethylene)]-(N-benzyloxycarbonyl -phenylalanine) benzyl ester (150 mg., 0.150 mmoles) in 4 ml. of ethanol:acetic acid (1:1), and the resulting mixture was hydrogenated for 12 hours at room temperature and 40 psi H$_2$. The mixture was then filtered and the filtrate concentrated to a solid (128 mg.), which was triturated with ether to yield a purified [N-(t-butyloxycarbonyl)-phenylalanine]histidine-statine-[amino(2-sec-butyl-ethylene]phenylalanine acetic acid salt solid product [109 mg.; 84% yield; m.p. 117°–126° C.; $R_f=0.57$ in BuOH-H$_2$O-AcOH (4:1:1); $^1$H-NMR (CD$_3$OD, 250 MHz): delta 0.8–1.0 (m, 12H, 1.36 (s, 9H), 1.92 (s, 6H), 2.2–2.45 (m, 2H), 4.28 (dd, J=9, 4, 1H), 3.54 (broad t, 1H), 6.92 (s, 1H), 7.2–7.4 (m, 10H), 7.63 (s, 1H)].

EXAMPLE 9

[N-(t-butyloxycarbonyl)-Phe]-His-Cyclostatine-Lys-Phe

A. N-(t-butyloxycarbonyl)-Cyclostatine

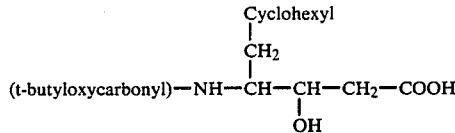

Glacial acetic acid (6.5 ml.) and 10% Rh/C catalyst (1.5 g.) were added to a solution of N-(t-butyloxycarbony) -4(S)-amino-3(S)-hydroxy-5-phenylpentanoic acid (10.02 g., 9.70 mmoles) in methanol (200 ml.), and the resulting mixture was hydrogenated for 8 hours at room temperature and 45 psi H$_2$. The reaction mixture was then filtered and the filtrate concentrated to a white solid, which was triturated in hexane to afford a purified product [8.46 g.; 83% yield; m.p. 109–110° C.; $R_f=0.72$ in CHCl$_3$ MeOH:Acetic acid, 18:2:1; $^1$HNMR (CDCl$_3$): 1.45 (s, 9H), 2.55 (d, J=6, 2H)].

B. Title Compound

In like manner to that described in Example 1, but using N-(t-butyloxycarbonyl)-cyclostatine in place of N-(t-butyloxycarbonyl)-statine, the title compound was prepared ($^1$NMR, CD$_3$OD, 1.50 delta, 9H s [BOC]).

EXAMPLE 10

[N-(t-butyloxycarbonyl)-Pro]-Phe-His-Cyclostatine-Lys-Phe

In like manner to that described in steps A to F of Example 1, but using N-(t-butyloxycarbonyl)cyclostatine in place of N-(t-butyloxycarbonyl)statine, the compound histidine-cyclostatine-(N-epsilon -benzyloxycarbonyl-lysine)-phenylalanine benzyl ester dihydrochloride was prepared. In like manner to that described in steps G and H of Example 1, but using [N-(t-butyloxycarbonyl)-proline]-phenylalanine (which is commercially available) in place of N-(t-butyloxycarbonyl) -phenylalanine and using 95:5 CHCl$_3$:MeOH as the silica gel chromatography eluant, the title compound was prepared as a purified solid product ($^1$NMR, CD$_3$OD, 1.49 delta, 9H s [BOC]).

EXAMPLE 11

[N-(t-butyloxycarbonyl)-Phe]-His-Cyclostatine-[Amino(2-sec butyl-ethylene)]-Phe Acetic Acid Salt In like manner to that described in Example 8, but using N-(t-butyloxycarbonyl)-cyclostatine in place of N-(t-butyloxycarbonyl)-statine, the title compound was prepared [m.p. 150 '163° C. (dec); $R_f=0.50$ in butanol:acetic acid:water, 4:1:1 (ninhydrin); $^1$H NMR (CD$_3$OD): 0.6–2.4 (m, 23H), 1.37 (s, 9H), 7.1–7.4 (11, H), 6.95 (s, 1H), 7.70 (s, 1H)].

EXAMPLE 12

[N-(t-butyloxycarbonyl)-Phe]-His-Cyclostatine-Lys-Sta

In like manner to that described in Example 1, but using statine benzyl ester hydrochloride in place of L-phenylalanine benzyl ester p-toluenesulfonate and N-(t-butyloxycarbonyl)-cyclostatine in place of N-(t-butyloxycarbonyl)-statine, the title compound was prepared ($^1$H NMR, CD$_3$OD, 1.5 delta 9H s [BOC]).

EXAMPLE 13

[N-(t-butyloxycarbonyl)-Phe]-His-Cyclostatine- (3-methoxycarbonyl -1,2,3,4-tetrahydro-2-Isoquinoline)

A.
[N-(t-butyloxycarbonyl)-Cyclostatine]-(3-methoxycarbonyl -1,2,3,4-tetrahydro-2-Isoquinoline)

In like manner to that described in Step C of Example 1, but using N-(t-butyloxycarbonyl)cyclostatine (190 mg., 0.60 mmole) in place of N-(t-butyloxycarbonyl) -statine and 3 methoxycarbonyl-1,2,3,4-tetrahydro isoquinoline hydrochloride (137 mg., 0.60 mmole) in place of (N-epsilon-benzyloxycarbonyllysine) -phenylalanine benzyl ester hydrochloride, the compound [N-(t-butyloxycarbonyl)-cyclostatine]-(3-methoxycarbonyl -1,2,3,4-tetrahydro-2-isoquinoline) was prepared as a foam which was used without further purification in the next step (301 mg., $^1$H NMR, CDCl$_3$, 1.5 delta 9H s [BOC]).

B. Title Compound

In like manner to that described in steps D to H of Example 1, 391 mg of the compound [N-(t-butyloxycarbonyl) phenylalanine]-histidine-cyclostatine-(3-methoxycarbonyl -1,2,3,4-tetrahydro-2-isoquinoline) was prepared as a foam. This foam was purified by chromatography (silica gel, chloroform/methanol gradient) to afford 138 mg of purified product as a white solid (¹HNMR, CDCl₃, 1.5 delta, 9H R [BOC]).

EXAMPLES 14 to 18

In like manner to that described in Example 13, but using the appropriate derivative of isoquinoline, quinoline or piperidine in place of 3-methoxy-carbonyl1,2,3,4-tetrahydro-isoquinoline, the following compounds were prepared:

| [N—(t-butyloxycarbonyl)-Phe]—His—Cyclostatine-R¹ | |
|---|---|
| EXAMPLE | R¹ |
| 14 | 1,2,3,4-tetrahydro-2-isoquinolinyl |
| 15 | 3-aminocarbonyl-1,2,3,4-tetrahydro 2-isoquinolinyl |
| 16 | 1,2,3,4-tetrahydro-1-quinolinyl |
| 17 | 4 phenylmethyl-1-piperidinyl |
| 18 | 3-methoxycarbonyl-1,2,3,4,5,6,7,8-decahydro-2-isoquinolinyl |

EXAMPLE 19

[N-(t-butyloxycarbonyl)-Pro)-Phe-His-Cyclostatine(1,2,3,4-tetrahydro-2-Isoquinoline)

In like manner to that described in Example 14, but using [N-(t-butyloxycarbonyl)-proline]phenylalanine in place of N-(t-butyloxycarbonyl)phenylalanine, the title compound was prepared.

EXAMPLE 20

[N-(t-butyloxycarbonyl)-Phe]-His-Cyclostatine-Pro Methyl Ester

A [N-(t-butyloxycarbonyl)-Cyclostatine]-Proline methyl Ester

In like manner to that described in step C of Example 1, but using N-(t-butyloxycarbonyl)cyclostatine (3.15 g. 10 mmoles) in place of N-(t-butyloxycarbonyl) -statine and proline methyl ester hydrochloride (1.65 g., 10 mmoles) in place of (N-epsilon -benzyloxycarbonyl-lysine)-phenylalanine benzyl ester hydrochloride, the compound [N-(t-butyloxycarbonyl) -cyclostatine]-proline methyl ester was prepared as a solid (3.945 g.).

B. Title Compound

In like manner to that described in steps D to H of Example 1, the compound N-(t-butyloxycarbonyl)-phenylalanine)-histidine-cyclostatine-proline methyl ester was prepared.

EXAMPLE 21

[N-(t-butyloxycarbonyl)-Phe]N-methyl-His-cSta-Lys-Phe

A.
[N-Alpha-(t-butyloxycarbonyl)-N-epsilon-benzyloxycarbonyl-Lysine)-Phenylalanine Benzyl Ester N-hydroxybenzotriazole (162 mg., 1.2 moles), N-methyl-morpholine (101.2 mg., 1 mmole), L-phenylalanine benzyl ester p-toluenesulfonate (428 mg., 1 mmole), N-alpha-(t-butyloxycarbonyl)-N-epsilon-benzyloxycarbonyl-L-lysine (456 mg., 1.2 mmoles and 1-cyclohexyl-3-(2-morpholinoethyl) carbodiimide metho-p-toluene sulfonate (635 mg., 80% pure, 1.2 mmoles) were sequentially dissolved in methylene chloride (50 ml.) at 0° C. and the resulting solution stirred for 19 hours at 20° C. The reaction mixture was then washed consecutively with 75 ml. of 5.5% aqueous HCl. 75 ml. of saturated aqueous NaHCO₃ and 75 ml. of brine, and dried over anhydrous MgSO₄. After filtration and evaporation, 669 mg. of crude product was obtained as a foam (¹H NMR, CDCl₃, 1.5 delta, 9H s [BOC]). This crude product was used without further purification in the next step.

B.
[N-epsilon-benzyloxycarbonyl-Lysine)-Phenylalanine Benzyl Ester Hydrochloride

[N-Alpha-(t-butyloxycarbonyl)-N-epsilon-benzyloxycarbonyl-lysine-phenylalanine benzyl ester from step A (5.6 g., 1 mmole) was dissolved in 25 ml. of 4N HCl/dioxane at 20° C. The reaction mixture was stirred and monitored by TLC (ethyl acetate/hexane). Upon completion, the reaction mixture was sequentially washed three times with ether, recrystallized in 10 ml of boiling nethylene chloride and recrystallized with 30 ml of diethyl ether. The crystals were filtered, washed three times with cold 3:1 diethyl ether/methylene chloride, and dried at room temperature overnight to yield 4.51 g of a white powder.

C.
[N-(t-butyloxycarbonyl)-cyclostatine]-(N-epsilon-benzyloxycarbonyl-Lysine)-Phenylalanine Benzyl Ester (N-epsilon-benzyloxycarbonyl-lysine)-phenylalanine benzyl ester hydrochloride from step B (2.46 g., 4.44 mmol), N-(t-butyloxycarbonyl)-statine (1.4 g., 4.44 mmol), N-hydroxybenzotriazole (1.021 g., 6.66 mmol) morpholinoethylcyclohexylcarbodiimide (1.980 g., 4.44 mmol), and triethylamine (0.801 ml., 5.77 mmol) were sequentially dissolved in 10 ml. of methylene chloride at 0° C. The reaction mixture was then allowed to stir at room temperature overnight. The resulting solution was then worked up as in step A to yield 4.22 g. of a pale yellow solid. ¹H NMR, CDCL₃, 250 mHz, partial, 1.45 (s, 9H, Boc), 0.8–1.9 (overlapping m), 2.2–2.5 (m, 2H), 3.05–3.2 (m, 4H), 3.6 3.92, 4.0 4.35, 4.72, 4.88 and 5.0 (m, 1H ea), 5.0–5.2 (m, 4H), 6.45 and 6.55 (d, 1H ea), 7.03 (m,2 H), 7.2–7.5 (m, aromatic).

D.
Cyclostatine-(N-epsilon-benzyloxycarbonylLysine)-Phenylalanine Benzyl Ester Hydrochloride

[N-(t-butyloxycarbonyl)-statine)-(N-epsilon-benzyloxycarbonyl-lysine)-phenylalanine benzyl ester from step C(2.144 g., 2.63 mmol) was dissolved in 4N HCl/dioxane and allowed to stand for one hour at 20° C. This reaction mixture was worked up as in step B to yield 1.80 g of a white powder. ¹H NMR, DMSO-d₆, 250 mHz, partial, 0.7–0.9 (m, 2H), 1.0–1.8 (m, 12–14H), 2.38 and 2.57 (dd, 1H ea), 2.9–3.1 (m, 4–5H), 3.2, 3.9, 5.63 (m, 1H ea), 4.25 and 4.52 (dt, 1H ea), 5.0–5.2 (m, 4H), 7.1507.45 (m, ca 13H), 7.82 (br, 3H), 8.2 and 8.52 (d, 1H ea).

E. [N-Alpha-(t-butyloxycarbonyl)-N-im-(t-butyloxycarbonyl)-N-methyl-Histidine)-cyclostatine-(N-epsilon -benzyloxycarbonyl-Lysine)-phenylalanine Benzyl Ester a. N-Methyl-L-Histidine methyl ester dihydrochloride One gram of N-methyl-L-histidine was dissolved in methanol and HCl was bubbled in at 0° C. for a few minutes. The mixture was heated at reflux for 1.5 hours (more hydrochloric acid was introduced on several occasions) and the cooled solution was concentrated at reduced pressure. HPLC indicated about 7% of unreacted starting material remaining. $^1$H NMR, DMSO-d$_6$, partial, 300 mHz, 2.62 (s, 3H, N-CH$_3$), 3.73 (s, 3H, OCH$_3$), 3.37 (AB doublets, 2H, superimposed on H$_2$O resonance), 4.48 (t, 1H), 7.51 (s, 1H, imidazolyl H-4), 7.98 (s, 1H, imidazolyl H-1).

b.
N-t-butyloxycarbonyl-Phenylalanine-N-methylHistidine methyl ester

N-Methyl-L-histidine methyl ester (1.05 g.) from step a was dissolved in dichloromethane and at 0° C., 1.25 ml of triethylamine was added, followed by N-t-butyloxycarbonyl-L-phenylalanine (1.14 g.), 1-hydroxybenzotriazole hydrate (1.04 g.) and dicyclohexylcarbodiimide (0.89 g.) the mixture was stirred at 0° C. and allowed to slowly warm to 20° C. over a 4–5 hour period. It was then stirred an additional 10 hours. The slurry was filtered, concentrated, redissolved in 100 ml of ethyl acetate, the additional precipitate was filtered, and the filtrate was washed with 1N sodium hydroxide (2×10 ml) dried over magnesium sulfate, and concentrated to give 0.84 g. of an off-white solid. Recrystallization of this material from ethyl acetate gave 0.47 g. of the title compound as a colorless powder. Additional material was obtained as follows. The combined filtered drying agent and second (from ethyl acetate) precipitate above were heated in methanol, and the resultant suspension was cooled, filtered and the filtrate was concentrated to give a solid which was chromatographed on silica in ethanol-dichloromethane to give 0.857 g. of the pure title substance. $^1$H NMR, CDCl$_3$, 250 mHz, partial, 1.39 (s, 9H, Boc), 2.80 (S, 3H, N-CH$_3$), 2.90 and 3.03 (m), 3.35 (m, 1H), 3.70 (s, 3H, OCH$_3$), 4.75 (dt, 1H), 5.15 (dt, 1H), 5.3 (d, BOCNH), 6.84 and 7.68 (1H ea, imidazolyl CH), 7.1–7.4 (m, aromatic). Singlets at 7.55 and 6.74 suggested about 10% of the substance exists in another rotameric form (imidazolyl CH resonances).

c. N-t-butyloxycarbonyl-Phenylalanine
N-methyl-Histidine-im-butyloxycarbonyl

The product of step (b), 2.32 g. was dissolved in acetone (70 ml) and water (20 ml) and the solution was cooled to 0° C. and treated with 5.4 ml of 1N sodium hydroxide. After 3.3 hours at 0° C. and fifteen hours at −20° C., the mixture was partially concentrated, and the remaining aqueous solution was adjusted to pH 5.8 with 1N hydrochloric acid. The free acid did not precipitate, so the pH was adjusted to 11 with 6N sodium hydroxide and the volume was adjusted to 30 ml with water. 30 ml of dioxane was added, and the mixture while being cooled at 0° C. was treated with 1.61 ml of di-t-butylcarbonate while the pH was kept between 9 and 11 with added 6N sodium hydroxide. After about 1 hour at 0° C., the cooling bath was removed and 0.5 ml di-t-butylcarbonate was added. Fifteen minutes later the mixture was partially concentrated, extracted with ethyl acetate, washed with water, the aqueous layers separated, combined, mixed with fresh ethyl acetate and brought to pH 1.4 with 6N hydrochloric acid at 0° C. The layers were separated, the organic layer was washed with water, dried over sodium sulfate and concentrated. The resultant oil was homogenized as an amorphous foam (1.9 g.) by several coevaporations with added ether. The title substance was over 95% pure by RP-HPLC. $^1$H NMR, CDCl$_3$, 250 mHz, partial, 1.38 and 1.35 (s, 9h total, Boc of rotational isomers), 1.60 and 1.69 (imboc, 9H total), 2.82 and 2.98 (s, 3H total, N-CH$_3$), 3.32 and 3.10 (AB d, 1H ea), 4.83(dt, 1H), 5.27 (m, 1H), 5.42 and 5.48 (d, 1H total, Boc NH), 7.1–7.35 (m, aromatic), 7.93 and 8.08 (s, 1H total, imidazolyl H-2).

d. Title Compound (E)

0.976 g. (1.37 mmol) of cyclostatine-(N-epsilon-benzyloxycarbonyl-lysine)phenylalanine benzyl ester hydrochloride from step D, 0.799 g (1.55 mmol) of N-t-butyloxycarbonyl from step d, 0.310 g (1.55 mmol) of dicyclohexylcarbodiimide,0.247 ml of triethylamine, and 0.378 g (2.47 mmol) of hydroxybenzotriazole were sequentially dissolved in 3.0 ml of methylene chloride at 0° C. and stirred at 0° C. for 20 hours. The reaction mixture was worked up as in step A to yield 0.930 g of a white foam. $^1$H, NMR, DMSO-d$_6$, 250 mHz, partial, 1.24, 1.28, and 1.32 (s, 9H total, isomeric Boc), 1.44, 1.48, and 1.52 (s, 9H total, isomeric imboc), 2.76, 2.96, and 3.02 (s, isomeric N—CH$_3$), 2.90 (m, 2–4 H), 3.82, 3.86, 4.52, 4.80 (m, 1H ea), 4.95–5.10 (m, 4H, CH$_2$O), 7.15–7.45 (m, aromatic), 7.72, 7.84, 8.45 (m, 1H ea), 8.04 and 8.10 (s, 1H total, imidazolyl H-2).

F.
[N-Alpha-(t-butyloxycarbonyl-phenylalanine)-N-im-(t-butyloxycarbonyl)-N-methyl-Histidine)cyclostatine-Lysine-phenylalanine 470 mg (0.387 mmol) of the [N-Alpha-(t-butyloxy -carbonyl)-N-methyl-Histidine)-cyclostatine-(N-epsilon-benzyloxycarbonyl-Lysine)-phenylalanine benzyl ester from step E, and 80 mg of 20% Pd(OH)$_2$/C catalyst were sequentially added to 20 ml of methanol and 2 ml of acetic acid. The reaction mixture was then filtered through Super-Cel, concentrated and evaporated to dryness to yield 377 mg. of a white powder. $^1$H NMR, DMSO-d$_6$, 250 mHz, partial, 1.29, 1.27, and 1.25 (s, 9h total, isomeric Boc), 1.42, 1.48, and 1.50 (s, OH total, isomeric imBoc), 2.75, 2.95, and 3.02 (s, isomeric N—CH$_3$), 4.22, 4.52, 5.05, 5.25, 7.66, 7.84 (m, 1H ea), 7.0–7.3 (m, aromatic), 7.32 and 7.42 (s,1H total, isomeric imidazolyl H-4), 8.03 and 8.10 (s, 1H total, isomeric imidazolyl H-2).

G. Title Compound 358 mg (0.341 mmol) of the product of step F and 94 mg (0.682 mmol) potassium carbonate were added to 20 ml of methanol. The reaction was complete in 2.5 hours at which point was added 200 ml of acetic acid. The reaction mixture was then concentrated to one ml., 150 ml. of acetic acid and 1 ml of 0.1M, pH 4.3 ammonium acetate were then added to the reaction mixture. The isomers were then separated by High Pressure Liquid Chromatography. The L-histidine isomer was then triturated to yield a white powder ($^1$H NMR, 250 MHZ, DMSO-d$_6$ partial 2 (ppm from TMS), 1.30 (s, 9H BOC), 2.86 and 3.05 (s, 3H, total N-CH$_3$), 6.75 and 6.85 (s, 1H total, imidazolyl H$_4$ of two rotational isomers), 7.51 (imidazolyl H-2).

EXAMPLE 22

[N-(t-butyloxycarbonyl]-Phe-]-N-methyl-His-Sta-Ile-Phe

A. N-im-(t-butyloxycarbonyl)-N-methyl-Histidine

N-methyl-Histidine (prepared by the procedure of J. Med. Chem. 1968 11 258-60 (600 mg., 2.93 mmol), triethylamine (1.65 ml 11.2 mmol), t-butyloxycarbonyl (1.48 ml, 6.4 mmol), 10% sodium bicarbonate (8.5 ml) and 2N HCl (10 ml) were dissolved in 5 ml dimethylformanide. After completion of the reaction, the dimethylformanide was evaporated, 15 ml of ethyl acetate and 15 ml of 10% sodium bicarbonate solution were added. The mixture was washed with ethyl acetate (2×5 ml), acidified with 2N HCl (8 ml), extracted with ethyl acetate (4×20 ml) washed with brine and dried to yield 846 mg of a foam. $^1$H NMR, 60 mHz, CDCl$_3$, partial, 1.4 (s, 9H, Boc), 1.6 (s, 9H, Boc), 2.8 (s, 3H, N—CH$_3$), 2.85 (m, 1H), 3.15 (m, 1H), 4.75 (m, 1H) 7.2 and 8.1 (s, 1H ea, imidazolyl CH).

B. [N-im-(t-butyloxycarbonyl)-N-methyl Histidine]-Sta Ile-Phe-benzyl ester 179 mg (0.43 mmol) of Statine-Isoleucine Phenylalanine benzyl ester hydrochloride, 316 mg (0.65 mmol) of N-im-(t-butyloxycarbonyl)-N-methyl histidine from step A, 91 ul of triethylanine, 165 mg (1.07 mmol) of hydroxybenzotriazole, and 134 mg (0.65 mmol) of dicyclohexylcarbodiimide were combined in 8 ml of methylene chloride. Upon completion of the reaction (~7 hr), the reaction mixture was diluted with methylene chloride, filtered, concentrated, extracted with ethyl acetate (40 ml), filtered, washed with 1N NaOH (2×5 ml), washed with brine and dried over sodium sulfate to yield 235 mg (62% yield) of a foam. $^1$H NMR, 250 mHz, CDCl$_3$, partial, 0.82 (m, 12H), 1.45 (s, 9H, Boc), 1.60 (s, 9H, imBoc), 1.80, 2.33, 2.52, 2.91, 3.24, 3.67, 4.05, 4.25, 6.82 (m, 1h each), 2.93 (s, 3H, N—CH$_3$), 3.12 (m, 2H), 4.8–5.0 (m, 2H), 5.13 (AB doublets, CH$_2$O), 7.0–7.4 (m, 12–15H), 7.96 (s, 1H, imidazolyl H-2).

C. N-methyl-His-Sta-Ile-Phe benzyl ester hydrochloride

The product of step B (228 mg 0.26 mmol) was dissolved in 4N HCl/dioxane to yield the title compound. $^1$H NMR, 250 mHz, DMSO-d$_6$, partial, 0.7–0.95 (m, 12H), 3.03 (m, 2H), 3.8 (m, 2H), 4.25 (m, 2H), 4.55 (m, 1H), 5.05 (AB doublet, 2H, OCH$_2$), 7.1–7.4 (m, ca. 12H), 7.50 (s, 1H, imidazolyl H-4), 7.85 (d, 1H), 8.6 (m, 2H), 8.8 (br, 1H).

D.
[N-(t-butyloxycarbonyl)-Phe]-N-methyl-His-Sta-Ile-Phe-benzyl ester

The product of step C (100 mg, 0.133 mmol), t-butyloxycarbonyl-phenylalanine (41 mg, 0.154 mmol), triethylamine (50 ul, 0.35 mmole), hydroxybenzotriazole (35 mg, 0.231 mmol), and dicyclohexylcarbodiimide (32 mg, 0.154 ml) were combined in 1 ml of methylene chloride and 1 ml of dimethylformamide. Upon completion of the reaction, the reaction mixture was worked up as in Example 22 to yield 74 mg (57% yield) of a solid. $^1$H NMR, 250 mHz, CDCl$_3$, partial, 0.75–0.95 (m, 12H), 1.35 and 1.40 (s, 9H total, nonequivalent Boc in two rotameric forms), 3.0 (s, N—CH$_3$), 3.13 (m, 2–3H), 3.95, 4.25, 4.8, and 4.9 (m), 5.10 (AB doublet, (OCH$_2$, 2H), 6.7 (br, 1H), 7.0–7.4 (aromatic M).

E. Title Compound

By following the procedure of steps E to G of Example 21, the title compound was obtained. ($^1$H NMR, CD$_3$OD, 250 MHz partial, S(ppm from TMS); 0.90 (9H, Ml) 1.37 and 1.45 (S, 9H total BOC), 2.71, 3.06 (S, 3H total, N—CH$_3$), 4.22 (d, 1H), 7.1–7.3 (m, aromatic, 10–12H).

EXAMPLE 23

[N-(t-butyloxycarbonyl)-Phe-]-N-methyl-His-cyclostatine-Lys-Sta.

A. N-(t-butyloxycarbonyl)-statine benzyl ester

N-(t-butyloxycarbonyl)-statine (1141 mg., 5.12 mmol) were dissolved in 20 ml of dimethylformamide. 708 mg. of potassium carbonate and 0.609 ml of benzyl bromide was then added. After the reaction was complete, the reaction mixture was concentrated, taken up in ethyl acetate, washed twice with 5 ml of H$_2$O, dried over MgSO$_4$, filtered and concentrated to yield 1510 mg of a yellow oil (81% yield). $^1$H NMR, 90 mHz, CDCl$_3$, partial, 0.92 (d, J=7 Hz, 6H), 1.42 (s, 9H, Boc), 2.58 (m, 2H), 4.05 (m, 1H), 4.72 (d, BocNH, 1H), 5.13 (s, CH2O, 2H), 7.3 (s, 5H, aromatic).

B. Statine benzyl ester hydrochloride 1490 mg (4.08 mmol) of N-(t-butyloxycarbonyl)statine benzyl ester from step A were dissolved in 5 ml of 4N HCl/dioxane. The dioxane was stripped off with diethyl ether, and the reaction mixture was dried at 50° C. to yield 1230 mg of a yellow oil. $^1$H NMR, DMSO-d$_6$, 300 mHz, partial, 0.84 (d, 6H), 1.42, 1.72 (m, 1H), 2.6 (dd, 1H), 2.78 (dd, 1H), 3.1 (m, 1H), 4.03 (m, 1H), 5.14 (s, 2H, CH$_2$O), 5.82 (m, 1H), 7.4 (m, 5H), 8.02 (m, 3H).

C.
[N-Alpha-(t-butyloxycarbonyl)-N-epsilon-(benzyloxycarbonyl)-Lysine]-Statine benzyl ester 1200 mg (3.98 mmol) of the statine benzyl ester hydrochloride from step B, 8 ml of triethylamine, 1510 mg (5.17 mmole) of N-t-(butyloxycarbonyl-N-(benzyloxycarbonyl-Lysine (Chemalog), 977 mg (6.37 mmol) of hydroxybenzotriazole and 821 mg (3.98 mmole) of dicyclohexylcarbodiimide were added sequentially to 8 ml of methylene chloride at 0° C. After the reaction was complete, the reaction mixture was worked up on in Example 21 to yield 1770 mg (71% yield) as a white foam. $^1$H NMR, 300 mHz, CDCl$_3$, partial, 0.92 (d, 6H), 1.42 (s, 9H, Boc), 2.54 (m, 2H), 3.20 (m, 2H), 4.00 (m, 3–4H), 5.14 (m, 4–5H), 6.36 (d, 1H), 7.4 (m, 11–13H).

D. N-epsilon-(benzyloxycarbonyl)-Lysine-Statine Benzyl Ester Hydrochloride 1760 mg (2.80 mmol) of the compound of step B was dissolved in 7 ml of 4N HCl/dioxane. The dioxane was stripped off, the reaction mixture was washed several times with diethyl ether, and dried over vacuum at 56° C. to yield 1550 mg of white foam. $^1$H NMR, 300 mHz, DMSO-d$_6$, partial, 0.86 (m, 6H), 1.36 (m, 4–6H), 1.72 (m), 2.4 (m, 2H), 2.96 (m, 3–4H), 3.8, 3.9 and 3.95 (m, 1H ea), 5.0–5.1 (m, 4–5H), 7.2–7.4 (m, 11–12H), 8.22 and 8.34 (m, 3–4H total), 8.50 and 8.84 (m, 1h ea).

E.
[N-t-butyloxycarbonyl)-cyclostatine]-N-epsilon-(benzyloxycarbonyl)-lysine-statine benzyl ester 1530 mg (2.77 mmol) of the compound of step D, 874 mg (2.77 mmol) N-(t-butyoxycarbonyl)-cyclostatine, 1533 mg (4.16 mmole) of hydroxybenzotriazole, 5.71 mg (2.77 mmol) of dicyclohexylcarbodiimide, and 0.50 ml (3.60 mmol) of triethylamine were added sequentially to 6 ml of methylene chloride at 0° C. The reaction mixture was stirred for 24 hours at 0° C. and worked up and concentrated to yield 1850 mg (82%) of a white foam. $^1$H NMR, DMSO-d$_6$, partial, 300 mHz, 0.90 and 0.94 (d, 6H total), 1.0–1.6 (various m), 1.38 (boc, s, 9H), 2.15–2.50 (m, 3H), 2.95 (m, 1H), 3.8 and 3.9 (m, 1H ea), 4.18 (m, 1H), 6.64 (d, 1H), 5.0–5.1 (m, 4.5H), 6.35 (d, 1H), 7.20 (m, 1H), 7.3–7.5 (m, aromatic), 7.9 (m, 1H).

F.

Cyclostatine-N-epsilon-(benzyloxycarbonyl)-lysine-statine benzyl ester hydrochloride 1830 mg (2.22 mmol) of the compound of step E was dissolved in 7 ml of HCl/Dioxane. The dioxane was stripped off with ether and the reaction mixture was worked up to yield 1740 mg of a pale yellow foam. $^1$H, NMR, 300 mHz, DMSO-$d_6$, partial, 0.90 and 0.94 (d, 6H total), 1.1–1.6 (m, 20–22H total), 2.1–2.6 (m, ca. 5H), 2.95 (m, 2H), 3.84 (m, 1H), 3.90 (m, 2H), 4.20 (m, 1H), 5.0–5.1 (m, 4–5H), 7.2–7.5 (m, aromatic), 7.6 (d, 1H), 7.8 (m, 2–3H), 8.18 (d, 1H).

G.

[N-Alpha-(t-butyloxycarbonyl-phenylalanine]N-methyl-im-(t-butyloxycarbonyl)-Histidine-cyclostatine-Lysine-Statine-Benzyl Ester 300 mg (0.416 mmol) of [N-alpha-(t-butyl oxycarbonyl)-N-methyl-im-(t-butyloxycarbonyl)-Histidine prepared according to the procedure of steps A to D of Example 22, 215 mg (0.416 mmol) of the compound of step F, 7.5 ml (0.541 mmol) of triethylamine, 96 mg (0.624 mmol) of hydroxybenzotriazole and 86 mg (0.416 mmol) of dicyclohexylcarbodiimide were sequentially dissolved in 3 ml of methylene chloride at 0° C. Upon completion of the reaction, the mixture was taken up in ethyl acetate, filtered, washed twice with 1 ml of 1N NaOH, once with 1 ml of brine and dried over MgSO$_4$ to yield 341 mg of a white foam (89%). $^1$H NMR, 300 mHz, DMSO-$d_6$, partial, 0.88 (two d, 6H), 1.36 and 1.52 (s, 9H ea, Boc and imBoc), 2.6–3.2 (several m), 3.58, 3.84, and 4.46 (m, 1H ea), 4.0–4.2 (m, ca. 4H), 7.05 (d, 1H), 7.0–7.3 (m, aromatic), 7.56 (d, 1H), 7.96 (d, 1H), 8.07 (s, 1H, imidazolyl H-2), 8.28 and 8.52 (d, 1H ea).

H.

[N-alpha-(t-butyloxycarbonyl)-phenylalanine-N-methyl-im-(t-butyloxycarbonyl)-Histidine-cyclostatine-Lysine-Statine 326 mg of the compound of step G, and 75 mg of Pd(OH)$_2$/C catalyst were added to 11 ml of a 10:1 methanol/acetic acid solution. Upon completion, the reaction mixture was filtered through Super-Cel, concentrated, washed three times with toluene, worked up with diethyl ether and dried over high vacuum to yield 255.4 mg (91%) of a white foam. $^1$H, NMR, DMSO-$d_6$, 250 mHz, partial, 0.82 (two d, 6H total), 1.24, 1.28 1.34, 1.40, 1.48, and 1.52 (isomeric Boc and imBoc singlets), 2.74, 2.98, and 3.00 (isomeric N—CH$_3$), 7.06–7.4 (m, aromatic), 7.45 (s, one of isomeric imidazolyl H-4), 8.03 and 8.10 (s, 1H total, isomeric imidazolyl H-2).

I. Title Compound 254 mg (0.239 mmol) of the compound of step H, and 83 mg (0.60 mmol) of potassium carbonate were added to 2.0 ml of methanol to yield the title compound. (1H NMR, DMSO-D$_6$, 250 MHZ, partial, ppm from TMS: 1.35 (s, 9H, BOC), 0.9 (m, 6H, CH(CH$_3$)$_2$), 2.79 and 3.04 (s, 3H, N—CH$_3$ of rotational isomers), 6.89 (s, imidazolyl H-2), 7.2–7.4 (m, aromatic).

EXAMPLE 24

[N-alpha-(t-butyloxycarbonyl)-phenylalanine]-Histidine-cyclostatine-N-methyl-N-(3-dimethylaminoprop-1-yl) amide

A.

t-butyloxycarbonyl-cyclostatine-N-methyl-N-(3-dimethylaminoprop-1-yl)amide 142 mg (1.22 mmol) of 1-(N,N-dimethylamino)-3-(N'-methylamino)propane, 350 mg (1.11 mmol) of N-(t-butyloxycarbonyl)cyclostatine, 255 mg (1.66 mmol) hydroxybenzotriazole, and 2.29 mg (1.8 mmol) of dicyclohexylcarbodiimide were dissolved in 2 ml of methylene chloride at 0° C. After the reaction was complete, the reaction mixture was worked up as in Example 23 to yield 472 mg. of a yellow oil. $^1$H NMR, 300 mHz, CDCl$_3$, partial, 0.9 (m, 2H), 1.34 (s, 9H, Boc), 1.68 (m), 2.21 and 2.23 (s, 6H total, N(Me)$_2$), 3.40 and 3.33 (t, 1H ea), 3.64 (m, 1H), 4.01 (m, 1H), 4.82 (m, 1H, BocNH).

B.

Cyclostatine-N-methyl-N-(3-dimethylaminoprop-1-yl) amide dihydrochloride

The product of step A (452 mg, 1.09 mmol) was dissolved in 5 ml HCl/Dioxane. Upon completion, the reaction mixture was worked up as previously described to yield 470 mg (111% yield) of a yellow foam. $^1$H NMR, 300 mHz, DMSO-$d_6$, partial, 0.92 (m, 2H), 1.2–2.05 (several m, about 13H), 2.79 and 2.81 (s, 6H total), 2.92 and 3.08 (s, 3H total), 4.10 and 5.66 (m, 1 H ea), 8.02 (br, 3H).

C.

[C-(t-butyloxycarbonyl)-Phe]-N-im-(t-butyloxycarbonyl) His-cyclostatine-N-methyl-N-(3-dimethylaminoprop-1-yl)amide 440 mg (1.14 mmol) of the compound of step C, 573 mg (1.14 mmol) of t-butyloxycarbonyl-phenylalanine-histidine, 262 mg (1.71 mmol) of hydroxybenzotriazole, 235 mg (1.14 mmol) of dicyclohexylcarbodiimide, and 205 ul (1.48 mmol) of triethylamine were dissolved in 3 ml of methylene chloride. Upon completion, the reaction mixture was worked up as previously described to yield 790 mg (89%) of a yellow foam. $^1$H NMR, 250 mHz, CDCl$_3$, partial, 1.25 and 1.50 (s, 9H ea, Boc), 2.07 and 2,10 (s, 3H ea), 2.66 and 2.82 (s, 3H total), 3.8 (m, 2H), 4.1 (m, 1H), 4.55 and 4.8 (m, 1H ea), 7.0–7.4 (m, aromatic), 8.04 (s, 1H), 8.14 and 8.24 (m, 1H ea).

D. Title Compound

In a similar fashion to steps D-G of example 23 with the substitution of N-alpha-(t-butyloxycarbonyl)-phenylalanine-im-(butyloxycarbonyl) histidine in place of the N-methyl histidine compound and following the procedural steps, the title compound is obtained. ($^1$H NMR, DMSO-$d_6$, 300 MHz, partial (ppm from TMS); 1.30 (s, 9H, BOC), 2.88 (s), 2.96 (s), 3.26 (s), 6.88 (s, 1H), 7.58 (s, 1H), 7.2–7.3 (m, aromatic, 5–6H).

EXAMPLE 25

Inhibition of the Angiotensinogen-Cleaving Activity of Renin In vitro

Blood plasma was obtained from healthy laboratory personnel, pooled and stored frozen until required. Before use, a quantity of this plasma was defrosted and centrifuged, and the supernatant mixed with protease inhibitors and buffered to pH 7.4. Renin inhibitors were added at different levels to different aliquots of the plasma supernatant, and the resulting mixtures (310 lambda) incubated for three hours at 37° C. along with renin inhibitor-free control mixtures. After incubation, the mixtures were quenched in ice water and each assayed for angiotensin I using angiotensin I antibody. The production of angiotensin I in the presence of a renin inhibitor was compared to that produced in the absence of the inhibitor, and a percentage inhibition was calculated. Using data obtained from duplicate incubations at each of several different inhibitor concentrations, the inhibitor concentration in the incubation mixture required to produce a fifty percent inhibition of the angiotensinogen-cleaving activity of renin, i.e. the IC$_{50}$ of the inhibitor, was calculated for various different inhibitors.

The angiotensin I in the quenched incubation mixtures was assayed by means of a radioimmunoassay, using components of a renin radioimmunoassay kit supplied by Becton Dickinson and Co. (Orangeburg, N.Y.). This radioimmunoassay was based upon the one developed by Haber et al., *J. Clin. Endocrinol.*, 29, pp. 1349–1355 (1969).

Using the foregoing procedure, renin inhibition coefficients were determined for the compounds prepared in each of Examples 1, 2, 3, 4, 5, 7, 8, 9, 10 and 11. In each case the experimental IC$_{50}$ value was less than 4 micromoles/liter.

EXAMPLE 26

Antagonization of Exogenous Renin-Induced Pressor Response In Vivo

Male Sprague-Dawley rats (230 to 300 g. body weight) are anesthetized with sodium pentobarbital (65 mg./kg. body weight, intraperitoneal), after which femoral vein and carotid artery catheters are implanted in each animal. Following completion of surgery, the animals are placed in the prone position and rectal temperature monitored continuously. Mean arterial blood pressure (MAP) is recorded via the carotid artery catheter using a Statham P23 ID pressure transducer and a physiograph. Subsequent to a stabilization period, control renin pressor responses (dP) of 20 to 30 mm Hg are obtained by administration of hog renin (30 to 80 mU/Kg. body weight, intravenous). After the MAP returns to the baseline, a renin inhibitor is administered (10 mg./kg. body weight, intravenous), the animals are rechallenged with hog renin (same dosage as for control response) at 5, 15 and 30 minutes after renin inhibitor administration and the corresponding renin pressor responses (dP) measured. Percent antagonization is calculated as $$\frac{(\text{Control } dP - \text{experimental } dP) \times 100\%}{\text{control } dP}$$

where control dP and experimental dP are the pressor changes in MAP before and after renin inhibitor administration, respectively. Preferably, at least three animals are used in each test, with results averaged.

Using the foregoing procedure, percent renin-induced pressor response antagonizations may be determined for the compounds of the invention.

We claim:

1. A compound of the formula:

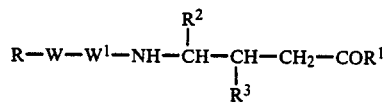

and the pharmaceutically acceptable salts thereof, wherein

R is hydrogen, an amino-protecting acyl moiety having a molecular weight of less than 500, proline, amino-protected proline, pyroglutamic acid or amino-protected pyroglutamic acid;

W is phenylalanine, histidine, leucine, tyrosine, or 1-naphthylalanine;

W$^1$ is phenylalanine, histidine, leucine, tyrosine, or norleucine, with the nitrogen of the peptide link between W and W$^1$ optionally being substituted by alkyl of from 1 to 4 carbon atoms when W is phenylalanine and W$^1$ is histidine;

R$^2$ is hydrogen, alkyl of from 1 to 6 carbon atoms, phenyl, cycloalkyl of from 4 to 7 carbon atoms, phenylalkyl of from 7 to 9 carbon atoms or cycloalkyl (alkylene) of from 5 to 10 carbon atoms;

R$^3$ is hydroxyl, amino, -NHR$^9$, NHCOR$^9$, OR$^9$, or OCOR$^9$, with R$^9$ being alkyl of from 1 to 4 carbon atoms; and R$^1$ is (a) -A-E-B, with A being lysine, proline, or additionally, when R$^3$ is amino or when the nitrogen of the peptide link between W and W$^1$ is substituted by alkyl of 1 to 4 carbon atoms, A is isoleucine.

E being phenylalanine, glycine, alanine, valine, isoleucine, lysine, ornithine, arginine, aspartic acid, gamma-esterified aspartic acid, glutamic acid or delta-esterified glutamic acid, B being -OR$^4$, NR$^4$R$^5$, glutamic acid, glutamic acid (—OR$^4$)$_2$, glutamic acid (—OR$^4$) (—NR$^4$R$^5$) or -glutamic acid (—NR$^4$R$^5$)$_2$, and R$^4$ and R$^5$ each being hydrogen, alkyl of from 1 to 4 carbon atoms, phenylalkyl of from 7 to 9 carbon atoms or cycloalkyl (alkyl) of from 5 to 10 carbon atoms,

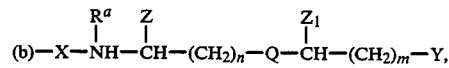

with X being absent or alanine, isoleucine, lysine, proline, ornithine, arginine, N-(Alkyl of from 1 to 4 carbon atoms)-lysine, N,N-di(alkyl of from 1 to 4 carbon atoms)-lysine, N-(alkyl of from 1 to 4 carbon atoms)-ornithine or N,N-di(alkyl of from 1 to 4 carbon atoms)-ornithine, R$^a$ being hydrogen or alkyl of from 1 to 4 carbon atoms, Z and Z$^1$ each being hydrogen, alkyl of from 1 to 6 carbon atoms, cycloalkyl of from 4 to 7 carbon atoms, cycloalkyl-(alkylene) of from 5 to 10 carbon atoms or phenylalkyl of from 7 to 9 carbon atoms, n and m each being 0 or an integer from 1 to 6, Q being

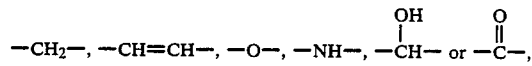

Y being methyl, phenyl, COOR$^6$, CONR$^6$R$^7$, —NH$_2$, (benzyloxy)carbonylamino, glutamic acid, —CO-glutamic —CO-glutamic acid (—OR$^6$)(NR$^6$R$^7$)$_2$, NR$^6$R$^7$, and R$^6$ and R$^7$ each being hydrogen, alkyl of from 1 to 4 carbon atoms, phenylalkyl of from 7 to 9 carbon atoms or cycloalkyl(alkylene) of from 5 to 10 carbon atoms,
(c) $NH_2$,
(d) alkoxy of from 1 to 4 carbon atoms,
(e) 4-benzylpiperazin-1-yl,
(f) 1,2,3,4-tetrahydroquinolin-1-yl,
(g) 1,2,3,4-tetrahydroisoquinolin-2-yl,
(h) 1,2,3,4-tetrahydro-3-aminocarbonyl-isoquinolin-2-yl,
(i) 1,2,3,4-tetrahydro-3-methoxycarbonyl-isoquinolin-2-yl,
(j) 1,2,3,4,5,6,7,8-decahydro-3-methoxycarbonylisoquinolin-2-yl,
(k) 2-methoxycarbonyl-pyrrolidin-1-yl,
(l) 2-aminocarbonyl-pyrrolidin-1-yl,
(m) 4-phenylmethyl-piperidin-1-yl,
(n) -proline-B with B being as defined above, or
(o) -lysine-B, with B being as defined above.

2. A compound of claim 1 wherein R is an amino-protecting acyl moiety having a molecular weight of less than 500 or amino protected proline, W is phenylalanine, $W^1$ is histidine and W and $W^1$ are bonded in a peptide link.

3. A compound of claim 2 wherein $R^2$ is isobutyl and $R^3$ is hydroxyl or amino.

4. A compound of claim 2 wherein $R^2$ is cyclohexyl(methylene) and $R^3$ is hydroxyl.

5. A compound of claim 3 wherein $R^1$ is lysine-E-B.

6. A compound of claim 4 wherein $R^1$ is lysine-E-B.

7. A compound of claim 5 wherein E is phenylalanine and B is hydroxyl or amino.

8. A compound of claim 6 wherein E is phenylalanine and B is hydroxyl.

9. A compound of claim 5 wherein R is t-butyloxycarbonyl.

10. A compound of claim 6 wherein R is t-butyloxycarbonyl.

11. A compound of claim 5 wherein R is N-(t-butyloxycarbonyl)-proline.

12. A compound of claim 6 wherein R is N-(t-butyloxycarbonyl)-proline.

13. A compound of claim 3 wherein $R^1$ is

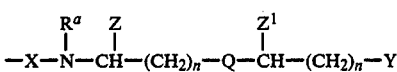

14. A compound of claim 4 wherein $R^1$ is

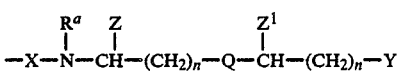

15. A compound of claim 13 wherein X is not absent.
16. A compound of claim 14 wherein X is not absent.
17. A compound of claim 15 wherein X is selected from the group consisting of alanine, proline, isoleucine and lysine.
18. A compound of claim 16 wherein X is selected from the group consisting of alanine, proline, isoleucine and lysine.
19. A compound of claim 17 wherein Z is isobutyl, Q is OH —CH—, $Z^1$ is hydrogen and n and m are each 0.
20. A compound of claim 18 wherein Z is isobutyl, Q is OH, $Z^1$ is hydrogen and —CH— n and m are each zero.
21. A compound of claim 19 wherein Y is selected from the group consisting of —$COOR^6$, —$CONR^6R^7$, glutamic acid, —CO— glutamic acid (—$OR^6$)$_2$, —CO— glutamic acid (—$OR^6$)(—$NR^6R^7$) and —CO— glutamic acid (—$NR^6R^7$)$_2$.

22. A compound of claim 20 wherein Y is selected from the group consisting of —$COOR^6$, —$CONR^6R^7$, glutamic acid, —CO— glutamic acid (—$OR^6$)$_2$, —CO— glutamic acid (—$OR^6$)(—$NR^6R^7$) and —CO— glutamic acid (—$NR^6R^7$)$_2$.

23. A compound of claim 18 wherein Z and $Z^1$ are each hydrogen, Q is —CH—, the sum of n and m is from 0 to 3 and Y is —$COOR^6$ or $CONR^6R^7$.

24. A compound of claim 18 wherein Z and $Z^1$ are each hydrogen, Q is —CH—, the sum of n and m is from 0 to 3 and Y is —$COOR^6$ or $CONR^6R^7$.

25. A compound of claim 19 wherein X is lysine.
26. A compound of claim 20 wherein X is lysine.
27. A compound of claim 21 wherein X is lysine.
28. A compound of claim 22 wherein X is lysine.
29. A compound of claim 23 wherein X is lysine.
30. A compound of claim 24 wherein X is lysine.
31. A compound of claim 13 wherein X is absent.
32. A compound of claim 14 wherein X is absent.
33. A compound of claim 31 wherein $Z^1$ is hydrogen, Q is —$CH_2$—, Y is —$COOR^6$, —$CONR^6R^7$, glutamic acid, —CO— glutamic acid (—$OR^6$)$_2$, —CO— glutamic acid (—$OR^6$)(—$NR^6R^7$) or —CO— glutamic acid (—$NR^6R^7$)$_2$, Z is alkyl of from 1 to 6 carbon atoms and the sum of n and m is from 0 to 3.

34. A compound of claim 32 wherein $Z^1$ is hydrogen, Q is —$CH_2$—, Y is —$COOR^6$, —$CONR^6R^7$, glutamic acid, —CO-glutamic acid (—$OR^6$)$_2$, —CO— glutamic acid (—$OR^6$)(—$NR^6R^7$) or —CO— glutamic acid (—$NR^6R^7$)$_2$, Z is alkyl of from 1 to 6 carbon atoms and the sum of n and m from 0 to 3.

35. A compound of claim 31 wherein Q is —NH—, m is zero, n is 0 or 1, Y is $COOR^6$, —$CONR^6R^7$, glutamic acid, —Co-glutamic acid (—$OR^6$), —CO— glutamic acid (—$OR^6$)($NR^6R^7$) or —CO— glutamic acid (—$NR^6R^7$)$_2$ and Z is alkyl of from 1 to 6 carbon atoms.

36. A compound of claim 32 wherein Q is —NH—, m is zero, n is 0 or 1, Y is $COOR^6$, —$CONR^6R^7$, glutamic acid, —CO— glutamic acid ($OR^6$)$_2$, —CO— glutamic acid (—$OR^6$)($NR^6R^7$) or —CO— glutamic acid (—$NR^6R^7$)$_2$ and Z is alkyl of from 1 to 6 carbon atoms.

37. A compound of claim 35 wherein Y is $COOR^6$ or —$CONR^6R^7$.

38. A compound of claim 36 wherein Y is —$COOR^6$ or —$CONR^6R^7$.

39. A compound of claim 31 wherein $Z^1$ is benzyl.
40. A compound of claim 32 wherein $Z^1$ is benzyl.
41. A compound of claim 33 wherein Z is sec-butyl.
42. A compound of claim 34 wherein Z is sec-butyl.
43. A compound of claim 31 wherein $R^a$ is methyl, Z and $Z^1$ are each hydrogen, n and m are each 0, Q is $CH_2$ and Y is $NR^6R^7$.

44. A compound of claim 32 wherein $R^a$ is methyl, Z and $Z^1$ are each hydrogen, n and m are each 0, Q is $CH_2$ and Y is $NR^6R^7$.

45. A compound of claim 2 wherein R is of the formula $$R^8-M-\overset{O}{\underset{\|}{C}}-\quad \text{or} \quad R^8-M-\overset{O}{\underset{\|}{C}}-\text{Proline},$$

with M being —O—, —$CH_2$—, —NH—, or —$SO_2NH$— and $R^8$ being alkyl of from 1 to 6 carbon atoms, phenyl, phenylalkyl of from 7 to 9 carbon atoms or cycloalkyl (alkyl) of from 5 to 10 carbon atoms.

46. A compound of claim 45 wherein R is N-(t-butyloxycarbonyl)-proline.

47. A pharmaceutical composition containing a renin inhibiting-effective amount of a compound of claim 1 as the essential active ingredient in a pharmaceutically acceptable carrier.

48. A method of treating renin-associated hyperaldosteronism, comprising administering to a patient in need of such a treatment, a therapeutically effective amount of a compound of claim 1.

49. A method for inhibiting the cleavage of angiotensin by renin in the body of a mammal comprising administering to a mammal in need of such treatment a renin inhibiting effective amount of a compound of claim 1.

* * * * *